US009127481B2

(12) United States Patent
Westra et al.

(10) Patent No.: US 9,127,481 B2
(45) Date of Patent: Sep. 8, 2015

(54) MECHANICAL BARRIER RECIPIENT VERIFICATION SYSTEM

(75) Inventors: Luke A. Westra, Chicago, IL (US); James C. Stango, Cumming, GA (US); Kyle A. Koning, San Luis Obispo, IL (US); Michael S. Rafferty, Madison, WI (US); Wayne M. Hansen, Poynette, WI (US); Roy E. McDaniels, Watertown, WI (US)

(73) Assignee: Typenex Medical, LLC, Chicago, IL (US)

( * ) Notice: Subject to any disclaimer, the term of this patent is extended or adjusted under 35 U.S.C. 154(b) by 397 days.

(21) Appl. No.: 13/540,467

(22) Filed: Jul. 2, 2012

(65) Prior Publication Data

US 2013/0168281 A1  Jul. 4, 2013

Related U.S. Application Data

(60) Provisional application No. 61/503,971, filed on Jul. 1, 2011.

(51) Int. Cl.
*E05B 65/48* (2006.01)
*E05B 37/00* (2006.01)
(Continued)

(52) U.S. Cl.
CPC ............. *E05B 37/0048* (2013.01); *E05B 37/02* (2013.01); *A61M 2205/6009* (2013.01);
(Continued)

(58) Field of Classification Search
CPC ..... E05B 37/02; E05B 37/04; E05B 37/0048; E05B 37/0058; E05B 65/62; E05B 73/0082; E05B 73/0005; B65D 50/00; B65D 50/02; A61J 1/00; Y10T 70/7322; Y10T 70/40; A61M 2205/6009

USPC ........... 70/14, 30, 63–67, 312–315; 220/210, 220/212; 215/206, 201, 228
See application file for complete search history.

(56) References Cited

U.S. PATENT DOCUMENTS 1,343,145 A * 6/1920 Kosich ............................ 70/312
2,267,374 A * 12/1941 Eber ................................. 70/5
(Continued)

FOREIGN PATENT DOCUMENTS

WO   00/13588   3/2000
WO   02/07800   1/2002
(Continued)

OTHER PUBLICATIONS

Darren Quick, "Lockey Bottle Lock puts a combination cork in it", http://t.co/0jc7egnU, Sep. 24, 2012, 5 pgs.

*Primary Examiner* — Christopher Boswell
*Assistant Examiner* — Morgan McClure
(74) *Attorney, Agent, or Firm* — Dicke, Billig & Czaja, PLLC

(57) ABSTRACT

A mechanical barrier recipient verification system including a combination lock assembly having a housing carrying a combination lock mechanism. The housing forms an aperture. The lock mechanism selectively receives and captures a post inserted through the aperture. Further the lock mechanism is configured to provide combination unset and set states; unlocked and locked positions; and correctly and incorrectly entered code arrangements. Following insertion of the post into the aperture and with the lock mechanism in the locked position, the post is retained by the lock mechanism regardless of the correctly or incorrectly entered code arrangement.

20 Claims, 31 Drawing Sheets

(51) Int. Cl.
*E05B 37/02* (2006.01)
*E05B 73/00* (2006.01)

(52) U.S. Cl.
CPC ......... *E05B37/0058* (2013.01); *E05B 73/0005* (2013.01); *E05B 73/0082* (2013.01); *Y10T 70/40* (2015.04); *Y10T 70/7322* (2015.04)

(56) References Cited

U.S. PATENT DOCUMENTS

| | | | |
|---|---|---|---|
| 3,200,868 A * | 8/1965 | Strayer | 383/86 |
| 3,287,839 A | 11/1966 | Rotwein | |
| 3,355,915 A | 12/1967 | Saunders | |
| 3,383,885 A | 5/1968 | Epstein | |
| 3,416,338 A * | 12/1968 | Gehrie | 70/312 |
| 3,445,021 A | 5/1969 | Johnson | |
| 3,843,007 A | 10/1974 | Meyer | |
| 4,111,018 A | 9/1978 | Pilvet | |
| 4,122,947 A | 10/1978 | Falla | |
| 4,164,320 A | 8/1979 | Irazoqui et al. | |
| 4,265,101 A | 5/1981 | Kaplan | |
| 4,302,956 A * | 12/1981 | McMorrow et al. | 70/312 |
| 4,366,684 A * | 1/1983 | Bako et al. | 70/68 |
| 4,366,685 A * | 1/1983 | Remington | 70/70 |
| 4,415,802 A | 11/1983 | Long | |
| 4,520,641 A * | 6/1985 | Bako | 70/312 |
| 4,615,191 A | 10/1986 | Grandy | |
| 4,678,458 A | 7/1987 | Fredeking | |
| 4,679,419 A | 7/1987 | Scelba | |
| 4,685,314 A | 8/1987 | Greenwalt et al. | |
| 4,751,830 A | 6/1988 | Cheng | |
| 4,787,222 A * | 11/1988 | Irazoqui et al. | 70/57 |
| 4,857,713 A | 8/1989 | Brown | |
| 4,953,900 A | 9/1990 | Pickett | |
| 5,181,407 A | 1/1993 | Wu | |
| 5,272,318 A | 12/1993 | Gorman | |
| 5,343,724 A | 9/1994 | Sornes | |
| 5,540,065 A | 7/1996 | Wyers | |
| 5,925,028 A | 7/1999 | Delvigo | |
| 5,934,120 A | 8/1999 | Kuo | |
| 5,947,937 A | 9/1999 | Urrutia et al. | |
| 6,058,876 A | 5/2000 | Keene | |
| 6,059,132 A | 5/2000 | Benjamin | |
| 6,519,569 B1 | 2/2003 | White et al. | |
| 7,252,204 B1 | 8/2007 | Small | |
| 7,347,841 B2 | 3/2008 | Elhadad et al. | |
| 7,434,430 B2 | 10/2008 | Huang | |
| 7,454,855 B2 | 11/2008 | Kotik et al. | |
| 7,490,766 B2 | 2/2009 | Auchinleck | |
| 7,490,767 B2 | 2/2009 | Auchinleck | |
| 7,600,648 B2 | 10/2009 | Hamer | |
| 7,668,731 B2 | 2/2010 | Martucci et al. | |
| 7,887,222 B2 | 2/2011 | Fanfa et al. | |
| 8,020,415 B2 | 9/2011 | Corbin et al. | |
| 2002/0011734 A1 | 1/2002 | Pickett | |
| 2005/0154368 A1 | 7/2005 | Lim et al. | |
| 2007/0012075 A1 | 1/2007 | Xiao | |
| 2007/0179448 A1 | 8/2007 | Lim et al. | |
| 2007/0191787 A1 | 8/2007 | Lim et al. | |
| 2007/0225653 A1 | 9/2007 | Lim et al. | |
| 2008/0053167 A1 | 3/2008 | Basche | |
| 2008/0115544 A1 | 5/2008 | Yang | |
| 2009/0018521 A1 | 1/2009 | Delvigo | |

FOREIGN PATENT DOCUMENTS

| | | |
|---|---|---|
| WO | 02/088498 | 11/2002 |
| WO | 2006046242 | 5/2006 |
| WO | 2009/087374 | 7/2009 |

* cited by examiner

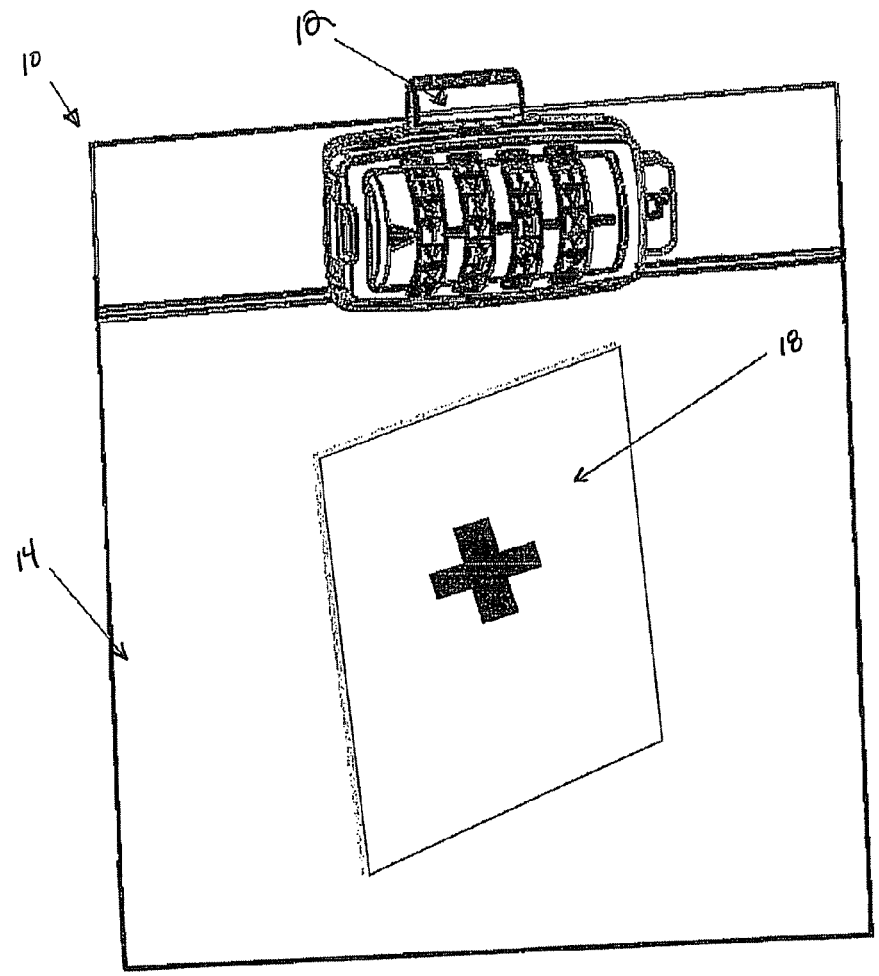
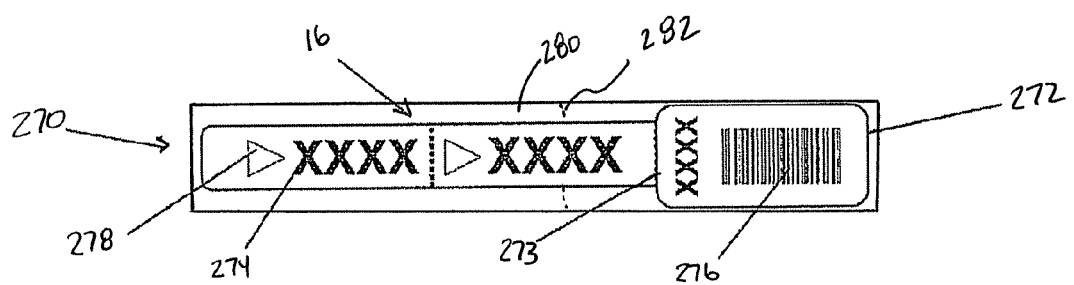
FIGURE 1

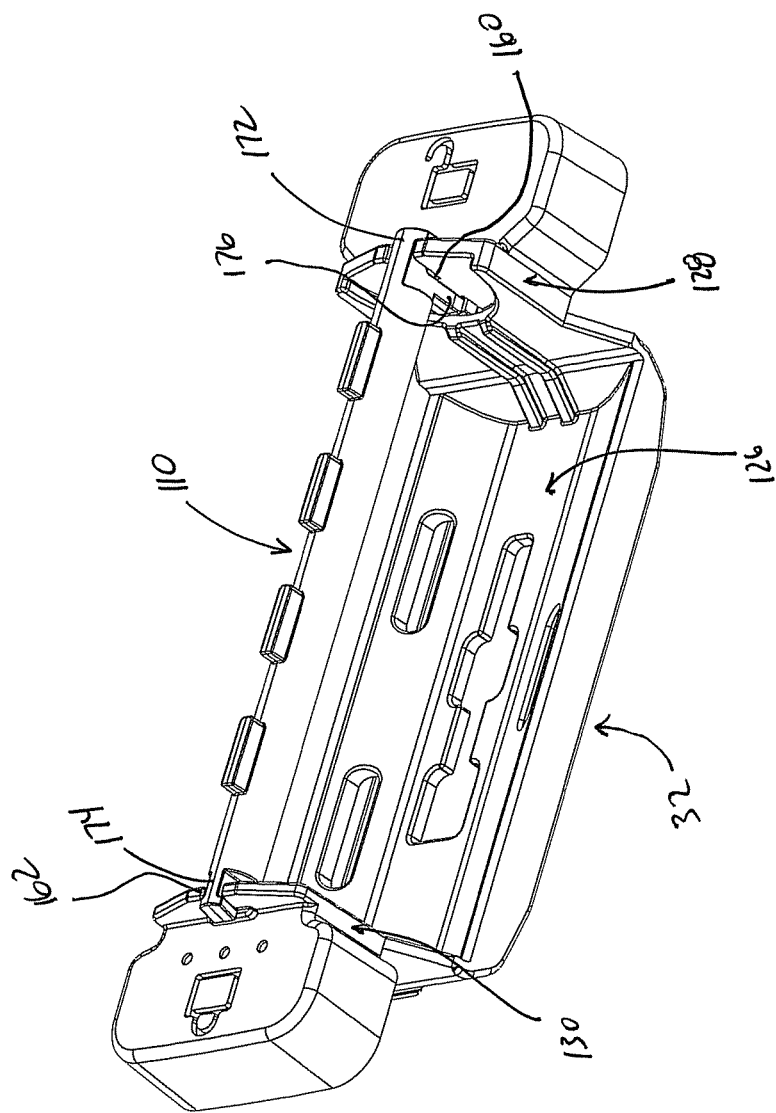

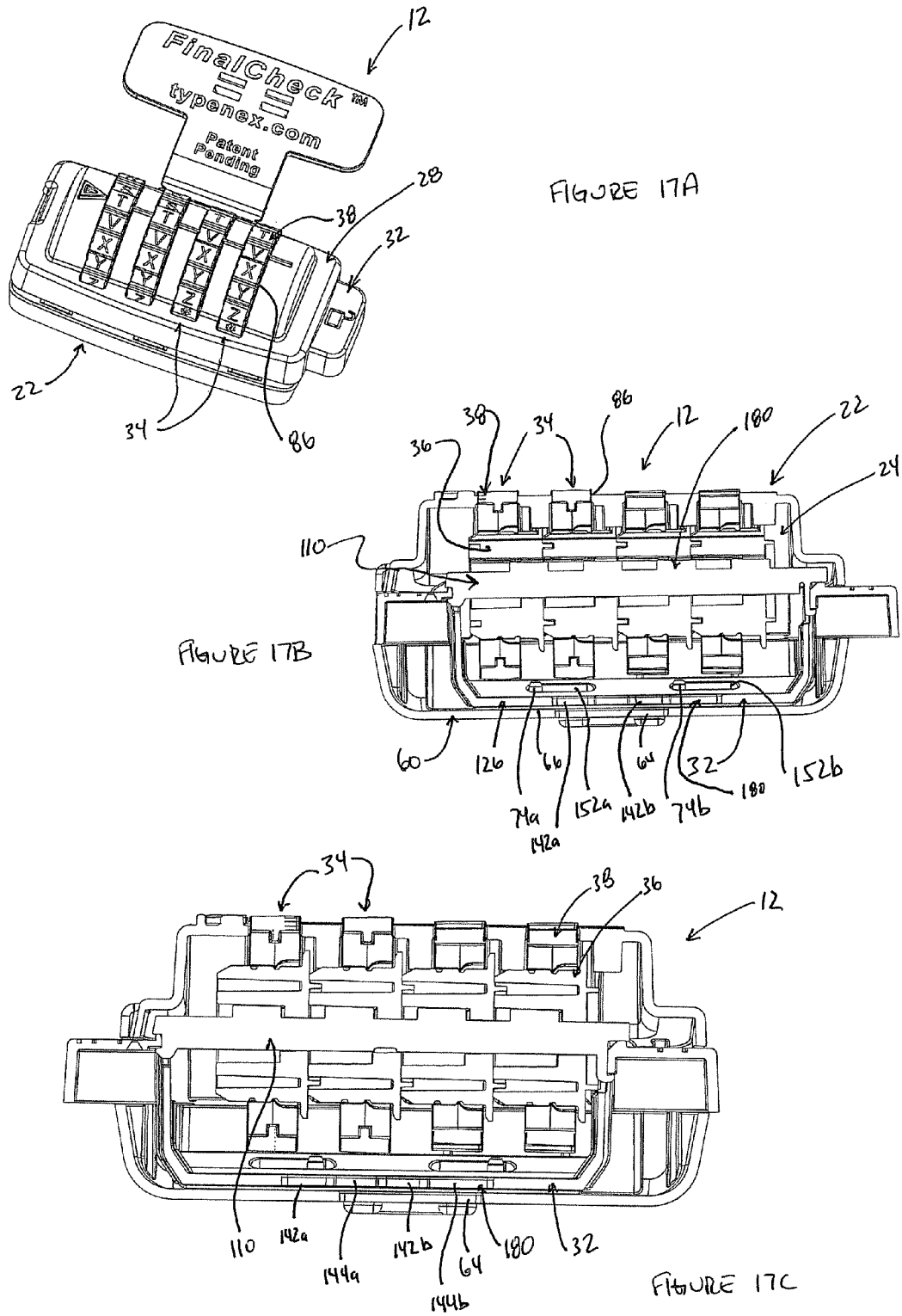

MECHANICAL BARRIER RECIPIENT VERIFICATION SYSTEM

CROSS-REFERENCE TO RELATED APPLICATION

This application claims priority under 35 U.S.C. §119(e)(1) to U.S. Provisional Patent Application Ser. No. 61/503,971, filed Jul. 1, 2011, entitled "Mechanical Barrier Recipient Verification System"; and the entire teachings of which are incorporated herein by reference.

BACKGROUND

The present disclosure relates to recipient verification and mechanical barrier systems, for example patient blood transfusion safety systems. More particularly, it relates to a recipient verification system capable of blocking handlers from accessing contents of a vessel without first entering a unique, recipient-specific code.

The need to assign a unique code or other identifier to a person or thing (collectively referred to as a "recipient") and subsequently employ the identifier in correlating other articles or activities to the recipient arises in a number of contexts. For example, positive patient identification is a critical step in providing medical treatment to patients in a caregiver environment (e.g., hospital). Commonly, an identification band is issued to the patient at the time of admission to the caregiver institution, and is worn by the patient at all times (e.g., a flexible plastic wristband or ankle band). The so-issued identification/admission band typically displays (e.g., printed or labeled) patient-related information, such as name, date of birth, etc. In some instances, a unique patient identifier or other code is assigned to the patient and is displayed on the band, including, for example, bar code or numeric/alphanumeric code. The patient identifier can alternatively be supplied on a separate band (apart from the admission band), and is used to cross-reference other caregiver-related items with the patient via, for example, an electronic data base. The unique patient identifier provides an independent, physical link to the patient. For example, paperwork or other caregiver documents/medical charts relating to the patient may include the patient identifier. In addition, the patient identifier can be applied to specimen samples (e.g., test tubes for blood specimens) taken from the patient, or applied to therapeutic material(s) to be given to the patient (e.g., blood donor units to be transfused), to better ensure that these and other items are accurately associated with the correct patient at all stages of the patient's visit with the caregiver institution. Along these same lines, similar recipient verification needs arise apart from hospital admission, for example blood banks, pharmacies, trauma centers, etc.

Upon issuance of therapeutic materials to be administered to the patient, the caregiver must accurately verify a match between the patient identifier on the therapeutic material(s) (e.g., either hand written on the materials or applied to the materials via an adhesive label) and the patient identifier on the intended recipient (e.g., affixed to the patient via a flexible plastic wristband or ankle band). This final recipient verification step is prone to error and can also be accidentally omitted from the process, thus allowing the administration of therapeutic materials to an incorrectly or unverified recipient.

Due to the error prone nature of this final recipient verification step, there is a need for a more active system to encourage the caregiver to match the patient identifier on the therapeutic materials and the patient. Current active systems either rely on electronic or manual systems. Both electronic and manual systems can incorporate a mechanical barrier system to restrict access to the therapeutic materials until a correct match of the patient identifier on both the patient and the therapeutic materials has been completed. Each type of system has unique advantages.

Manual recipient verification and mechanical barrier systems utilize a manual matching process where a human user must read and comprehend the codes and then confirm the match by performing an action (e.g., entering the patient identifier in to the mechanical barrier interface) before they can access the therapeutic materials to administer to the patient. This is currently accomplished by placing the therapeutic materials into a plastic polybag and then applying a mechanical combination lock to the opening of the bag to block access to the contents. Existing manual recipient verification and mechanical barrier systems provide a standalone system that can be accessed with no special tools or need for electricity or computer network connectivity.

The drawback of these current standalone manual systems is that the total number of unique patient identifier codes they are able to offer is limited by the number of code characters physically printed on the combination lock. Increasing the number of unique patient identifier codes available in the system before repeating codes increases the size of the combination lock and increases the complexity of the user interface. For example, current locks with a 3 alphabetic character code require a user to "dial in" each of those 3 characters to open the lock. If there are 24 characters to choose from and the lock is comprised of 3 wheels to enter the combination, each wheel would then have 24 characters. If it was desired to add a fourth character to the code, it would therefore be required to add a fourth wheel to the lock mechanism, again with all 24 characters on that fourth wheel. Thus, the total number of available codes for such a system is the same as the total number of physical combinations for the lock (in this case (characters)^(wheels)=24^3=13,824 unique codes in system).

Electronic recipient verification systems utilize elaborate electronics and software to automatically complete the verification of the patient identifier and thusly can provide a much greater number of unique codes because the user is not required to actually read the code or to manually enter the characters into the system to remove the mechanical barrier lock assembly and access the therapeutic materials. This approach results in a system that has a very large number of unique codes available, but also opens up the system to other issues. Electronic systems can require a complex system of networked computers, thus complicating the installation and adoption of such systems. In addition to the base technology needed for these systems there can also be issues of unplanned system downtime due to electrical power outages, lack of computer network connectivity and other causes that force the user to still have a manual process as a backup.

In light of the above, a need exists for a mechanical barrier recipient verification system exhibiting simplicity and low technology integrating cost and logistics of the manual system combined with the larger number of unique patient identifier codes than previously available in manual systems in a mechanism with no frangible component to be disposed of when initially setting the combination in to the lock. The system provides a simple-to-use lock assembly that functions in all situations, even electrical power outages.

SUMMARY

Aspects of the present disclosure relate to a mechanical barrier recipient verification system including a lock assembly, an optional overbag or other receptacle or vessel, and an optional label set or other article providing a unique identifier code. The lock assembly is mechanically-based, and provides unlocked and locked positions. In the unlocked position, the lock assembly permits access to an interior of the overbag and its contents, for example therapeutic materials maintained within the overbag. In some embodiments, the lock assembly is provided apart from the overbag, with the unlocked position further facilitating mounting of the lock assembly to the overbag. Regardless, to transition the lock assembly to the locked position, the unique identifier code is entered or set as the lock assembly's combination. In the locked position, the lock assembly prevents access to the overbag interior, and can only be transitioned to the unlocked position by entering of the unique identifier code. Systems of the present disclosure are thus highly useful for many, diverse end-use applications. For example, in the context of caregiver institutions where patient identification and verification is of great importance, the unique identifier code provided with the system is "assigned" to a particular patient (i.e., each patient at the caregiver institution is assigned a different unique identifier code). When a therapeutic material intended to be administered to the patient (i.e., the "intended patient") is prepared at a location remote from the intended patient (e.g., the caregiver's on-site laboratory), person(s) preparing the therapeutic material (e.g., a "delivering caregiver") have access to the unique identifier code assigned to the intended patient, and "set" the combination for the lock assembly to be the unique identifier code. The lock assembly is then "locked" to the therapeutic material-containing overbag, and the locked overbag is transferred to an administering caregiver located with a receiving patient. Normal caregiver protocols typically ensure that the receiving patient is, in fact, the intended patient. The systems of the present disclosure provide a more complete verification. In particular, in order to open the locked overbag and access the therapeutic material, the receiving caregiver reviews the identifier code assigned to the receiving patient, and attempts to open the lock assembly using this code. If so-entered combination is correct (i.e., the identifier code assigned to the receiving patient matches the combination set to the lock assembly using the identifier code of the intended patient), the lock assembly will open, providing a more complete verification that the receiving patient is, in fact, the intended patient. The therapeutic material can then be accessed and administered to the receiving/intended patient with confidence. Conversely, where the identifier code assigned to the receiving patient does not open the lock assembly, the receiving caregiver is immediately aware that the delivered therapeutic material may not have been intended for the receiving patient, and will undertake investigative efforts to verify.

The mechanical barrier recipient verification systems of the present disclosure optionally provide one or more advantages over existing systems. For example, a self-contained, one-time user-settable combination mechanism that allows for the user to set the combination without the need to dispose of a frangible component. Allowing for a greater number of unique identifiers to avoid potential repeat identifiers in caregiver institutions with a high volume of transactions. Providing a simpler user interface that requires fewer characters to be navigated to enter the combination character at each position. Requires no additional tools or mechanical aptitude to operate. Does not require external power or electricity or computer connection to operate and complete matching of the unique patient identifier.

BRIEF DESCRIPTION OF THE DRAWINGS

FIG. 1 is a perspective view of a mechanical barrier recipient verification system in accordance with principles of the present disclosure.

FIG. 9 is a perspective view of the slide bar of FIG. 7A assembled to a key pin component of the lock mechanism sub-assembly of FIG. 6.

FIG. 17A is a perspective view of the lock assembly of FIG. 6 upon final assembly.

FIG. 17B is a cross-sectional view of the lock assembly of FIG. 17A and illustrating an unlocked position.

FIG. 17C is a cross-sectional view of the lock assembly of FIG. 17A and illustrating a locked position.

DETAILED DESCRIPTION

Figure 2A:
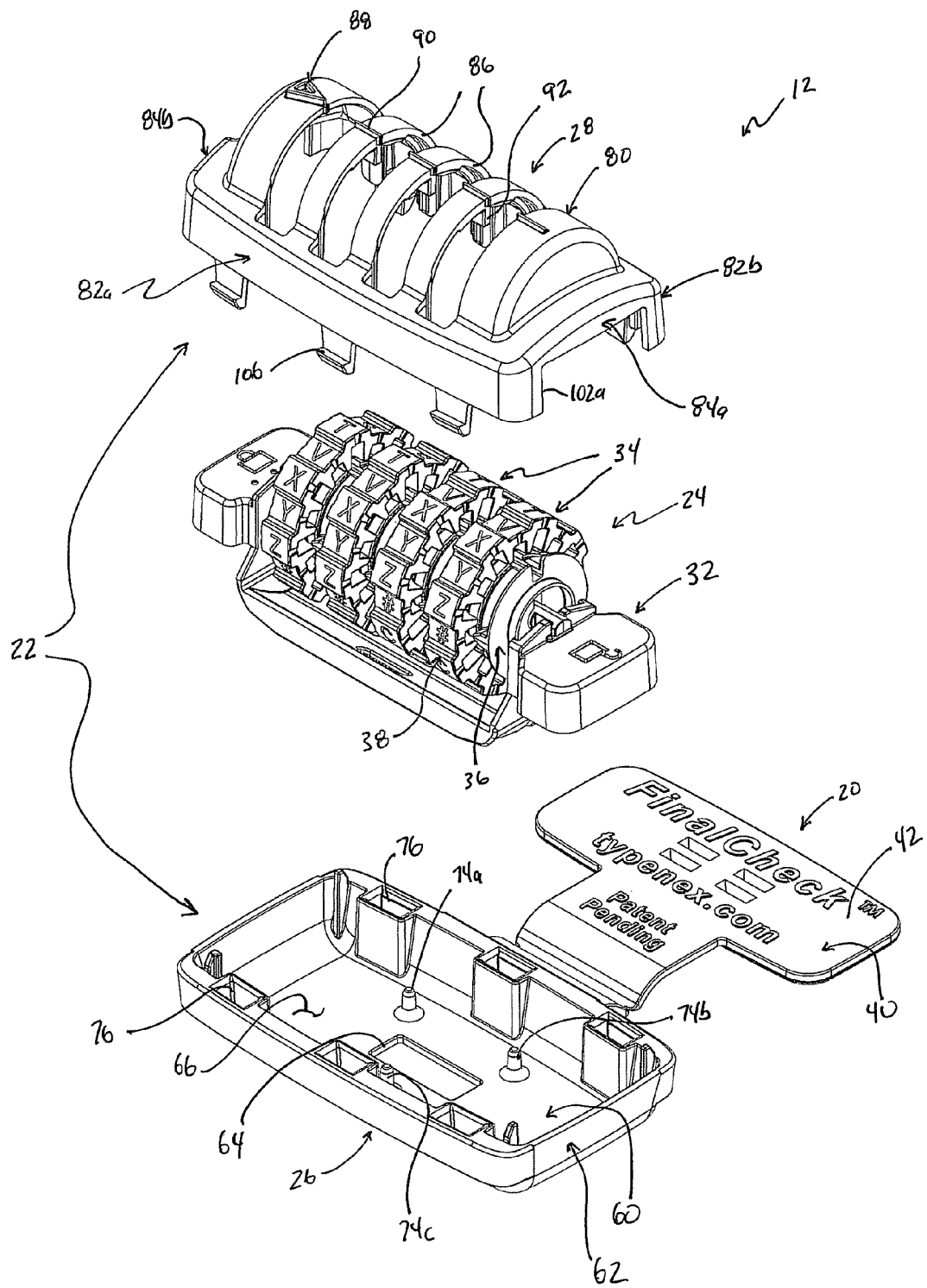
FIG. 2A is an exploded perspective view of a lock assembly in accordance with principles of the present disclosure and useful with the system of FIG. 1.

The present disclosure may be understood more readily by reference to the following detailed description taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Like reference numbers refer to like elements throughout the figures and prime numbers refer to alternate embodiments of such elements.

One embodiment of a mechanical barrier recipient identification system 10 in accordance with principles of the present disclosure is shown in FIG. 1. The mechanical barrier recipient identification system 10 includes a lock assembly 12, an overbag 14, and an article providing or displaying a unique identification code such as a unique identifier label set 16. Details on the various components are provided below. In general terms, however, the lock assembly 12 is configured to provide or operate in a combination unset state or combination set state, a correctly entered code arrangement or incorrectly entered code arrangement, and an unlocked position or a locked positions. The states, arrangements and positions are interrelated yet independent of another such that some or all of the states, arrangements and positions can exist in parallel. Broadly stated, in the combination set state and the incorrectly entered code arrangement, the lock assembly 12 cannot be transitioned from the locked position to the unlocked position. In the locked position, the lock assembly 12 is attached to, and prevents access to the contents of, the overbag 14. For illustrative purposes, the contents of the overbag 14 in FIG. 1 are represented as general therapeutic materials 18. Further, the overbag 14 is illustrated as a standard zip top polybag as known to those of ordinary skill. As described below, the unique identifier label set 16 (or other article) provides a unique code that can be used or "set" as the combination for the lock assembly 12. Thus, as initially provided to a user, the lock assembly 12 is in the combination unset state (e.g., various internal locking-related components are disconnected from one another, such that no combination for unlocking the lock assembly 12 has been established), and the user can establish the unique code as the lock assembly's 12 combination when transitioning to the combination set state. To summarize, the lock assembly 12 is initially provided to a first user in the combination unset state and the unlocked position, and is then transitioned to the set state to enter or assign the unique code as the lock assembly 12 combination (while remaining in the correctly entered code arrangement). Once in the combination set state, the lock assembly 12 cannot be re-transitioned back to the unset state. That is to say, the lock assembly 12 is, in some embodiments, configured to be a one-time, user-settable combination lock. The lock assembly 12 is then transitioned to the locked position and the incorrectly entered code arrangement, securing an interior of the overbag 14. Finally, to access an interior of the overbag 14, the lock assembly 12 can be transitioned to the unlocked position by a second user, but only if the unique code is properly entered by the second user (i.e., the second user first transitions the lock assembly 12 to the correctly entered code arrangement).

In some embodiments, the lock assembly 12 is configured for attachment to, and preventing access to the contents of, a vessel other than the overbag 14. Also, the unique code used as a combination for the lock assembly 12 can be provided or generated by component(s) unrelated to the label set 16. Thus, the overbag 14 and the label set 16 are optional components of the mechanical barrier recipient identification systems of the present disclosure.

In general terms, the lock assembly 12 incorporates various mechanical-based components that facilitate releasable mounting to the overbag 14 in a secured or locked manner. All components of the lock assembly 12 are preferably formed from plastic, although other materials can be used including rubber, metal, resin, composites, etc. also if deemed to be acceptable when considered by those skilled in the art.

Figure 2B:
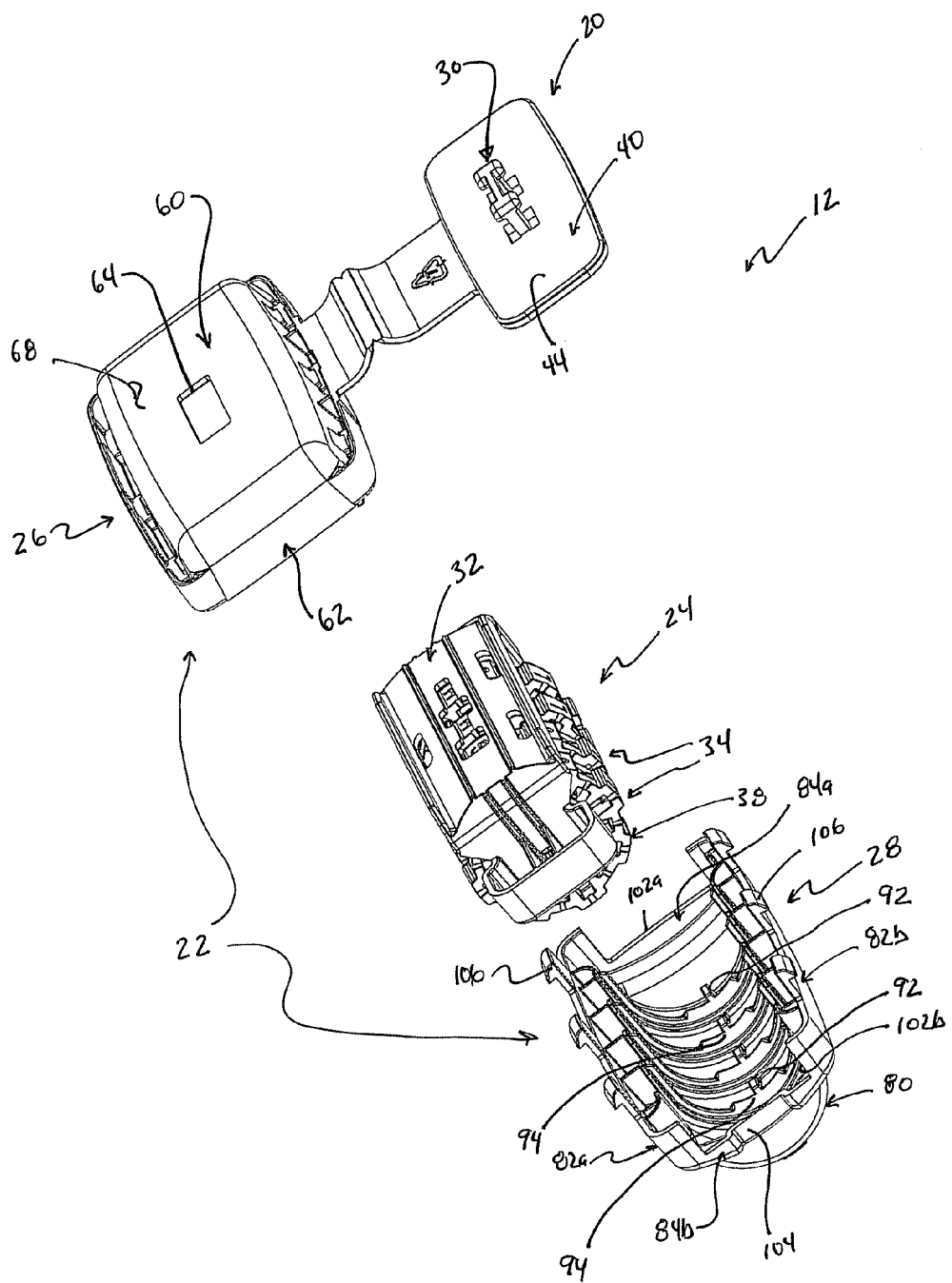
FIG. 2B is an exploded perspective view of the lock assembly of FIG. 2A from an opposite side.

One embodiment of the lock assembly 12 is shown in greater detail in FIGS. 2A and 2B, and includes an optional back plate unit 20, a housing 22 (referenced generally) and a lock mechanism sub-assembly 24. Details on the various components are provided below. In general terms, however, the housing 22 can be collectively defined by rear and front housing sections 26, 28, with the back plate unit 20 optionally connected to the rear housing section 26 and carrying a post 30 (visible in FIG. 2B). The lock mechanism sub-assembly 24 is carried by the housing 22 and is operable to selectively capture and release the post 30 relative to the housing 22. In this regard, the lock mechanism sub-assembly 24 includes a slide bar 32 (referenced generally) and one or more combination wheel pairs 34 (referenced generally) each including an inner wheel 36 and an outer wheel 38. The slide bar 32 is slidable relative to the housing 22 as permitted or prevented by a rotational position of the wheel pair(s) 34, with the post 30 being captured or released at the slide bar 32. A rotational position of the wheel pairs 34 at which sliding movement of the slide bar 32 is permitted (e.g., to release the captured post 30 in transitioning of the lock assembly 12 from the locked position to the unlocked position) is a pre-determined code or combination that can be established by a user, for example by referencing a code displayed on the label set 16, as described below.

Figure 3A:
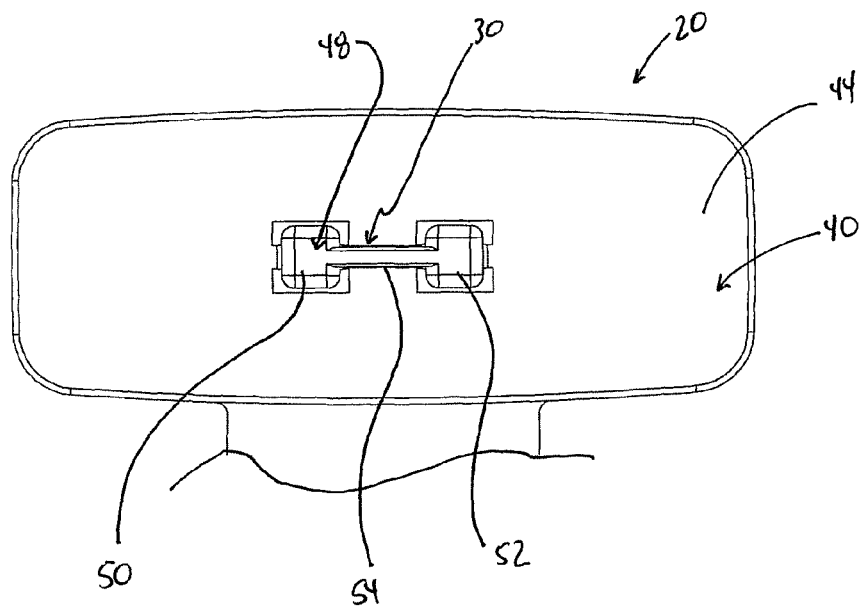
FIG. 3A is an enlarged top plan view of a back plate unit of the lock assembly of FIG. 2A.
Figure 3B:
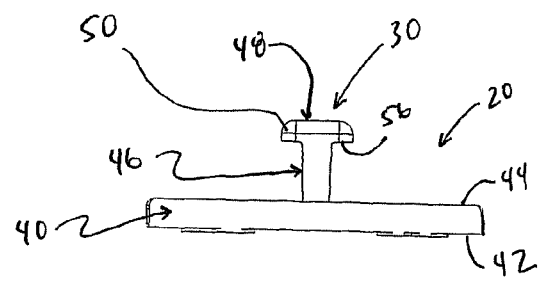
FIG. 3B is a side view of the back plate unit of FIG. 3A.

The back plate unit 20 includes the post 30 and a back plate 40. The back plate 40 forms or defines a leading face 42 (FIG. 2A) and a trailing face 44 (FIG. 2B). In some embodiments, at least the trailing face 44 can be substantially flat or planar (e.g., a surface flatness variation of no more than 10 percent). The post 30 projects from the trailing face 44 in a direction opposite the leading face 42, and has a size and shape corresponding with features associated with the other components of the lock assembly 12 for reasons described below. In some constructions, and with additional reference to FIGS. 3A and 3B, the post 30 includes a base 46 extending from the trailing face 44 and terminating in a head 48. A width of the head 48 is greater than that of the base 46 at first and second outer regions 50, 52, resulting in a dog bone-like shape as best reflected by FIG. 3A. That is to say, a smaller width intermediate region 54 is defined between the outer regions 50, 52. A wide variety of other shapes are also acceptable that may include only one, or more than two, of the enlarged regions 50, 52. Regardless, a ridge 56 (FIG. 3B) is defined along the outer regions 50, 52 as a lateral projection of the head 48 from the base 46 at a location transversely spaced from the trailing face 44. As described below, a size and shape of the head 48, and in particular the ridge 56, facilitates capturing and release of the post 30 by components of the lock mechanism sub-assembly 24 (FIG. 2A).

Returning to FIGS. 2A and 2B, the rear housing section 26 can assume various shapes and sizes appropriate for maintaining the lock mechanism sub-assembly 24 and for mating connection with the front housing section 28. The rear housing section 26 generally includes or defines a bottom wall 60 and a side wall 62 projecting outwardly about a perimeter of the bottom wall 60. An aperture 64 is defined through a thickness of the bottom wall 60 (i.e., the aperture is continuous through opposing inner and outer faces 66, 68 of the bottom wall). As reflected by FIG. 4, a size and shape of the aperture 64 correspond with a size and shape of the post 30, and in particular the head 48. More particularly, the aperture 64 is sized and shaped to permit the head 48 (including the enlarged outer regions 50, 52) to pass there through (e.g., a length and width of the aperture 64 is slightly greater than the corresponding maximum length and width of the head 48). Thus, in some embodiments the aperture 64 does not serve to capture the head 48, but instead serves to guide a user in correctly directing the post 30 into an interfacing relationship with the lock mechanism sub-assembly 24 (FIG. 2A) as described below. As further reflected by FIG. 4, in some configurations, the back plate 40 is connected to the rear housing section 26 by a connector body 70 that optionally forms a hinge 72, such as a living hinge. The connector body 70 maintains the post 30 in general alignment with the aperture 64 such that when a user presses the back plate 40 toward to the bottom wall 60 (such as during a vessel securing operation described below), the hinge 72 facilitates a pivoting-type motion, with the post 30 naturally being directed or guided toward the aperture 64. Other forms of the connector body 70 can also be employed that may or may not include the hinge 72. In yet other embodiments of the present disclosure, the connector body 70 is omitted, with the back plate unit 20 being separate from the rear housing section 26 (and other components of the lock assembly 12 (FIG. 2A)). In yet other embodiments, the post 30 is provided as an integral component of the vessel to be secured (e.g., the vessel can be a container, such as a cooler, having a projecting body akin to the post 30) such that back plate unit 20 is an optional component of the lock assemblies of the present disclosure and can be omitted.

Returning to FIG. 2A, one or both of the bottom wall inner and outer faces 66, 68 is substantially flat or planar (e.g., a surface flatness variation of no more than 10 percent). The rear housing section 26 optionally includes one or more additional features such as guide pins 74a-74c projecting outwardly from the inner face 66 of the bottom wall 60 for reasons made clear below. Further, one or more pockets 76 are formed along the side wall 62 that are configured to interface with corresponding features provided with the front housing section 28.

The front housing section 28 has or forms a top wall 80, opposing side walls 82a, 82b, and opposing end walls 84a, 84b. The side walls 82a, 82b and end walls 84a, 84b project from a perimeter of the top wall 80, with the top wall 80 having a curved (e.g., semi-cylindrical) shape. One or more slots 86 are formed through a thickness of the top wall 80, having a size and shape commensurate with corresponding ones of the wheel pairs 34 and in particular the outer wheel 38. That is to say, one of the wheel pairs 34 is associated with a respective one of the slots 86, with the slot 86 permitting the corresponding outer wheel 38 to rotate relative to the top wall 80; however, when nested within the slot 86, the corresponding outer wheel 38 is prevented from moving transversely relative to the front housing section 28. As described below, a portion of the outer wheel 38 is visible through the corresponding slot 86 upon final assembly, allowing a user to view an exterior of the outer wheel 38 when entering a code. In this regard, the top wall 80 optionally includes or forms one or more identifiers that visually indicate where, relative to the housing 22, the code should be "entered" at the outer wheel(s) 38. For example, the top wall 80 can form (e.g., molded, printed, labeled, etc.) primary alignment indicia 88 (visible in FIG. 2A) in the form of a triangle that "points" to a location at which a code should be "entered", and optionally one more secondary indicia 90 (e.g., raised "lines" that are aligned with the triangle indicia 88). The indicator(s) 88, 90 provided with front housing section 28 can assume a wide variety of other forms, and in other embodiments can be omitted.

Figure 5:
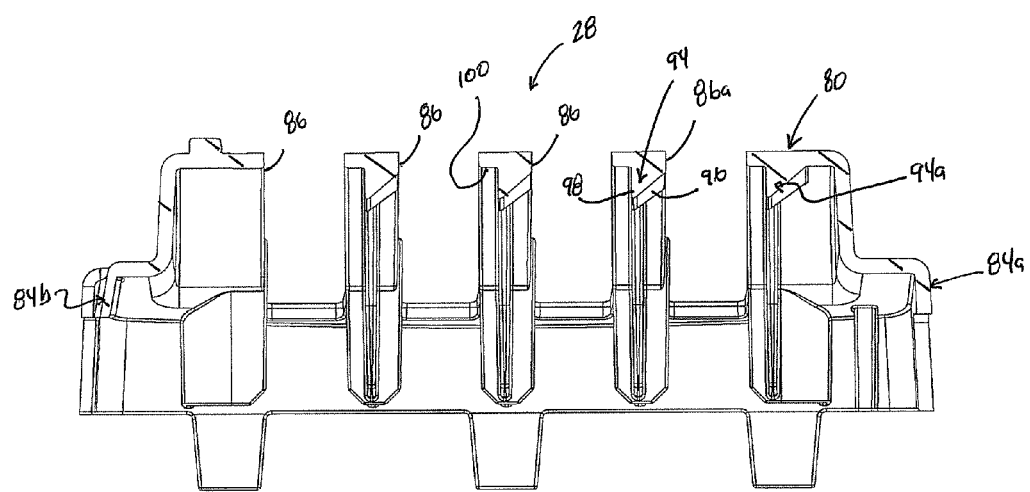
FIG. 5 is a cross-sectional view of a front housing section of the lock assembly of FIG. 2A.

As best shown in FIG. 2B, additional features can be formed or provided by the top wall 80 that facilitate operation of the lock mechanism sub-assembly 24. For example, an anti-rotation tab 92 can be formed as inward projection from the top wall 80 adjacent each of the slots 86 for reasons made clear below. Similarly, a ramp 94 can be formed adjacent each of the slots 86. The ramps 94 are shown in greater detail in FIG. 5, and are located between the first end wall 84a and the corresponding slot 86 (e.g., in the view of FIG. 5, the first ramp 94a is associated with the first slot 86a, and is located between the first end wall 84a and the first slot 86a). Each of the ramps 94 includes or defines a ramp surface 96 and a stop surface 98. Relative to an inner surface 100 of the top wall 80, the ramp surface 96 has an increasing inward projection in extension toward the corresponding slot 86. Stated otherwise, the ramp surface 96 tapers toward the inner surface 100 in extension from the stop surface 98 in a direction of extension toward the first end wall 84a.

Returning to FIGS. 2A and 2B, while the side walls 82a, 82b can extend relatively uniformly from the top wall 80, in some embodiments the end walls 84a, 84b each form a gap 102a, 102b sized and shaped in accordance with features of the slide bar 32. Further, a clearance notch 104 is defined along the second end wall 84b adjacent the corresponding gap 102b. As explained below, the optional gaps 102a, 102b facilitate slidable mounting of the slide bar 32 relative to the housing 22 in a manner permitting a user to visually see one or both ends of the slide bar 32 at different stages of operation. The optional clearance notch 104 further promotes visual perception of the slide bar 32 in a final set state and locked position.

In some embodiments, the front housing section 28 includes or forms one or more fingers 106 as extensions from the side walls 82a, 82b. The fingers 106 correspond in number and configuration with the pockets 76 described above. Thus, in some embodiments, assembly of the housing sections 26, 28 includes the fingers 106 snap-fitting into respective ones of the pockets 76. Alternatively, the housing sections 26, 28 can be assembled to one another in a wide variety of other manners that may or may not include the snap-fit fingers 106.

Figure 6:
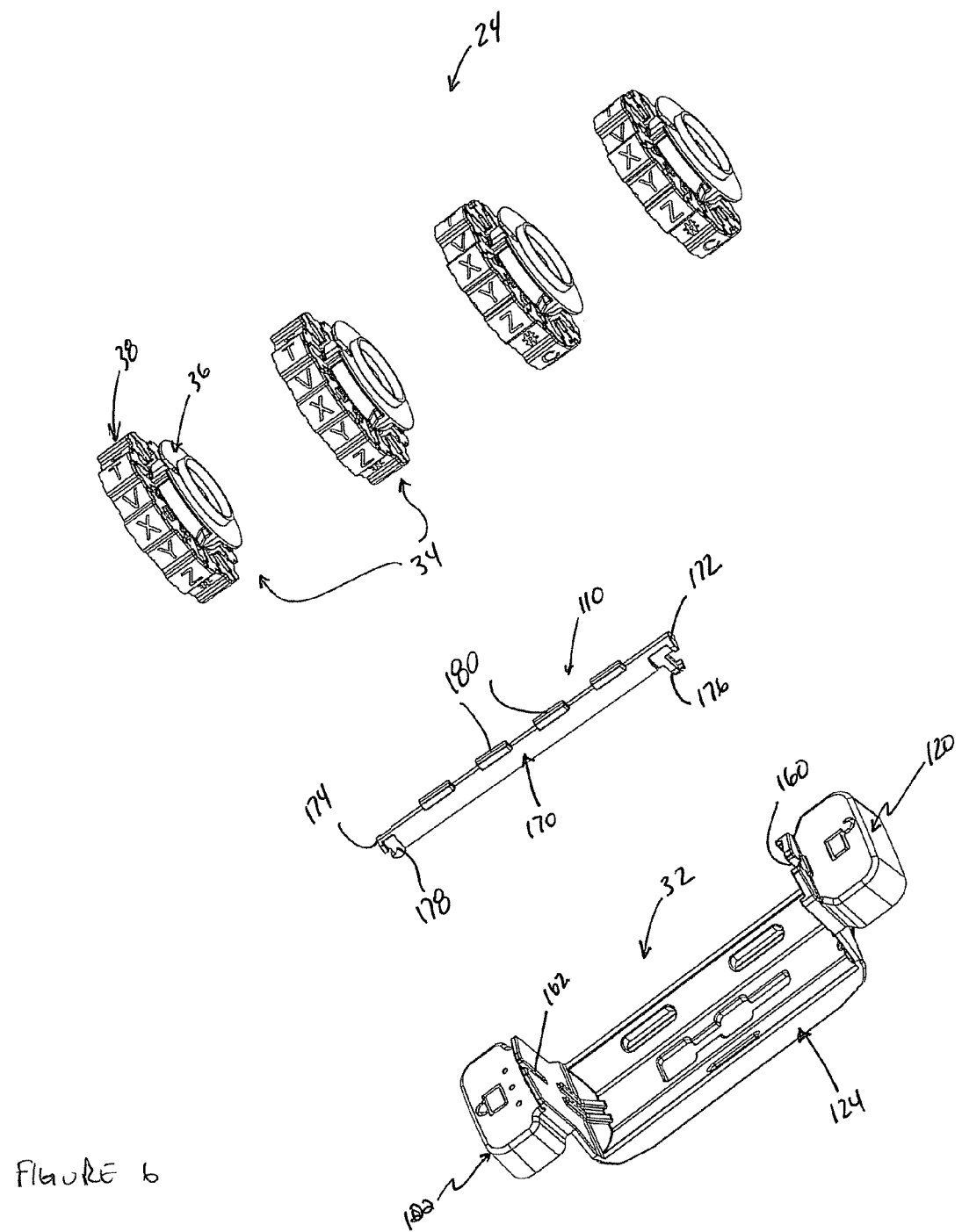
FIG. 6 is an exploded perspective view of a lock mechanism sub-assembly of the lock assembly of FIG. 2A.

The lock mechanism sub-assembly 24 is shown in greater detail in FIG. 6, and includes the slide bar 32, the one or more wheel pairs 34, and an optional key pin 110. In general terms, the wheel pairs 34 are rotatably disposed over the key pin 110, and the key pin 110 is mounted to the slide bar 32 in a manner permitting the wheel pair 34 to selectively rotate relative to the slide bar 32.

The slide bar 32 can be a homogenous (e.g., molded) body and generally defines opposing, first and second ends 120, 122, and an intermediate section 124. As better seen in FIG. 7A, in some embodiments the first and second ends 120, 122 each form a tab-like structure, whereas the intermediate section 124 includes a platform 126, and opposing, first and second end panels 128, 130. The end panels 128, 130 extend upwardly from the platform 126 at opposing ends thereof, and interconnect the corresponding end tab 120, 122 with the platform 126.

The end tabs 120, 122 can assume various shapes and sized, and in some embodiments are configured to be slidably received within a corresponding one of the front housing gaps 102a, 102b (FIGS. 2A and 2B). As made clear below, at least one of the end tabs 120, 122 is visible relative to the housing 22 (FIG. 2A) during use of the lock assembly 12 (FIG. 2a), and can be configured to provide a user with a visual indication as to an operational mode of the lock assembly 12. For example, the first end tab 120 can form or carry indicia 132 indicative of the unlocked position, and can be an icon representing the outline of an unlocked padlock. Conversely, the second end tab 122 can form or carry indicia 134 indicative of the locked position, and can be an icon representing the outline of a locked padlock. One or both of the indicia 132, 134 can assume a variety of other forms, such as one or more of letters, numbers, pictures, icons, etc. Further, and for reason made clear below, the second end tab 122 can form or carry confirmation indicia 136 (e.g., a series of dots as shown) adjacent the indicia 134.

Figure 4:
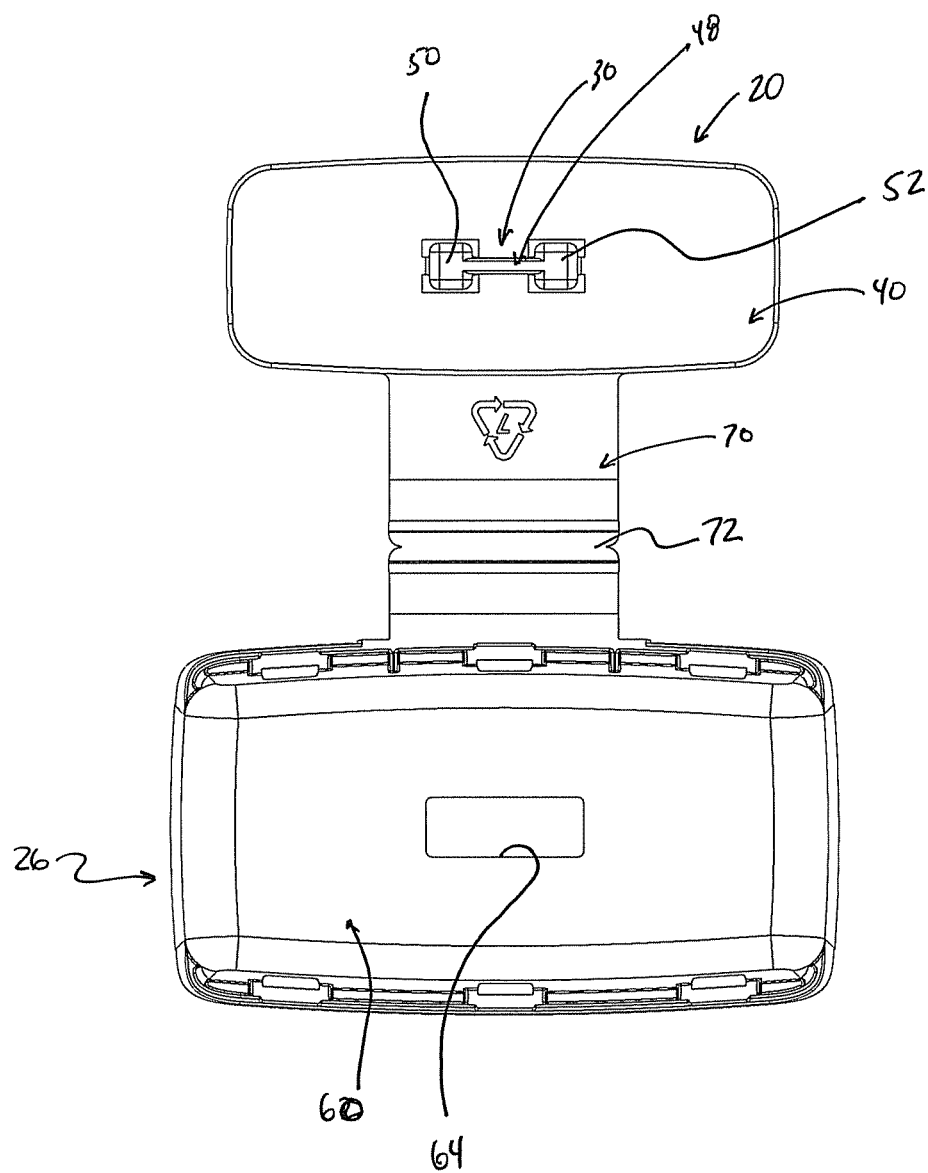
FIG. 4 is a rear plan view of a rear housing section of the lock assembly of FIG. 2A.

The platform 126 can be spatially offset from the end tabs 120, 122, and forms or defines a capture slot 140. The capture slot 140 extends through a thickness of the platform 126 (e.g., the capture slot 140 is open at opposing major surfaces of the platform 126 as reflected by FIGS. 7A and 7B), and is sized and shaped in accordance with the post head 48 (FIG. 4). For example, the capture slot 140 includes or defines one or more clearance segments 142a, 142b and one or more engagement segments or locking tabs 144a, 144b. With cross-reference between FIGS. 4 and 7A, the clearance regions 142a, 142b are larger than the engagement regions 144a, 144b (at least in terms of width), and are sized and shaped to allow passage of a corresponding one of the enlarged regions 50, 52 of the post head 48. Conversely, the engagement segments or locking tabs 144a, 144b are sized to prevent passage of the enlarged regions 50, 52, yet permit sliding of movement of the post base 46. With this construction, when the post 30 is arranged relative to the capture slot 140 such that the enlarged regions 50, 52 are aligned with corresponding ones of the clearance segment 142a, 142b, the post head 48 can freely be inserted into and removed from the capture slot 140 as reflected by FIG. 8A. Further, when the post head 48 is inserted into the capture slot 140 followed by transverse movement of the slide bar 32 relative to the post 30 (e.g., sliding of the slide bar 32 relative to the back plate 40 (FIG. 2A)), the engagement segments 144a, 144b are brought into alignment with corresponding ones of the enlarged regions 50, 52 as shown in FIG. 8B (it being understood that the first engagement segment or locking tab 144a is hidden in the view of FIG. 8B). With this arrangement, the ridge 56 of the head 48 abuts the platform 126 as shown in FIG. 8C, thereby capturing the post 30 relative to the slide bar 32. The post 30 can be released from the platform 126 by transversely moving the slide bar 32 relative to the post 30 in an opposite direction (i.e., returning to the arrangement of FIG. 8A). Thus, the engagement segments 144a, 144b can also be referred to as locking tabs. A variety of other configurations can be employed to effectuate selective capturing of the post 30 relative to the slide bar 32.

Returning to FIG. 7B, the platform 126 can be configured to provide a sliding interface with the rear housing inner face 66 (FIG. 2A). For example, the platform 126 can form or provide one or more ribs 150 that can easily slide along the inner face 66. Other constructions are equally acceptable that may or may not include the ribs 150. Other features, such as guide slots 152a-152c configured to slidably receive a respective one of the guide pins 74a-74c (FIG. 2A), can optionally be formed or provided by the platform 126.

Figure 7A:
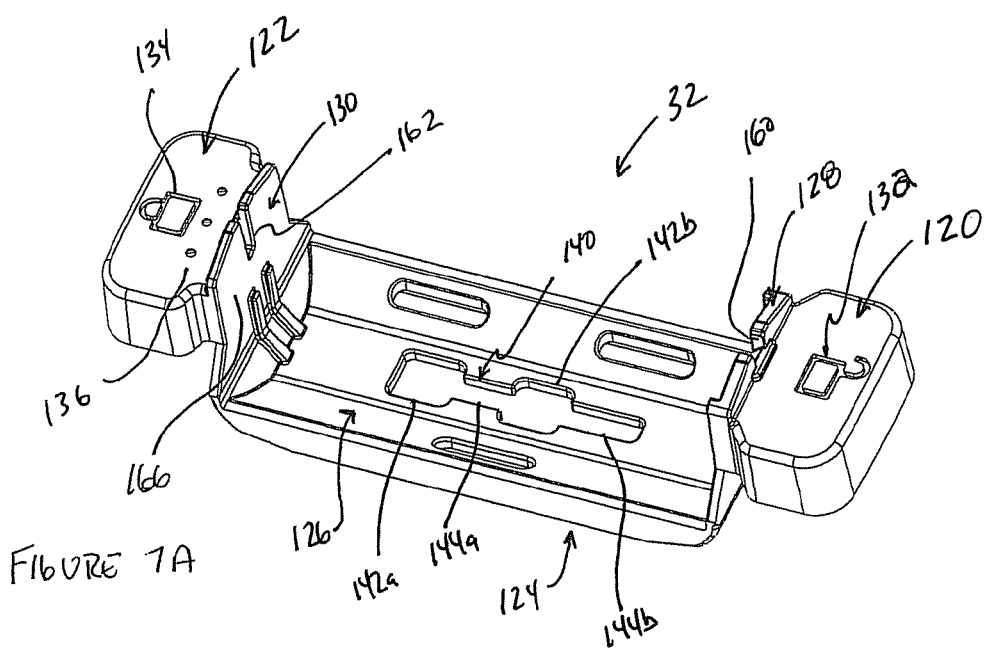
FIG. 7A is a top perspective view of a slide bar component of the lock mechanism sub-assembly of FIG. 6.
Figure 7B:
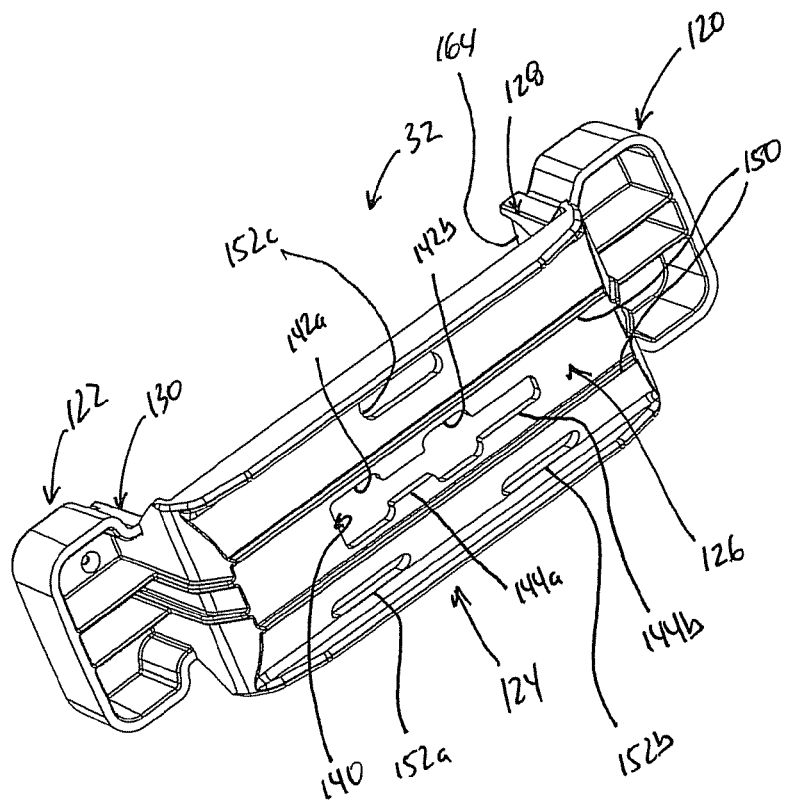
FIG. 7B is a bottom perspective view of the slide bar off FIG. 7A.
Figure 8A:
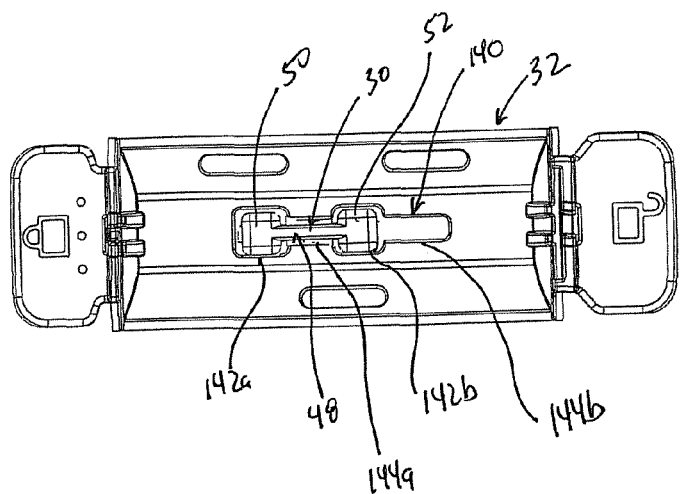
FIGS. 8A-8C illustrate a relationship between a post of the back plate unit of FIG. 3A with the slide bar of FIG. 7A.
Figure 8B:
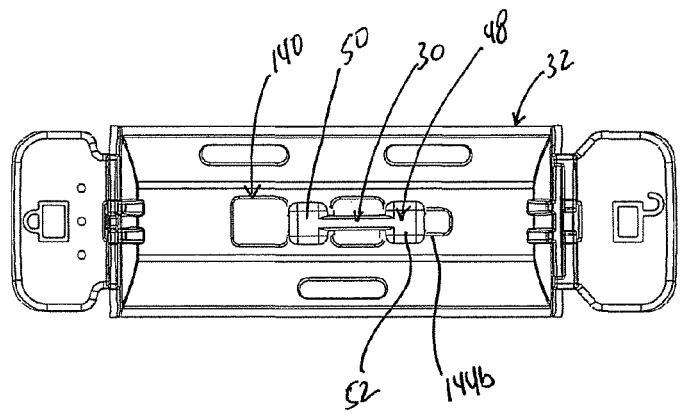
Figure 8C:
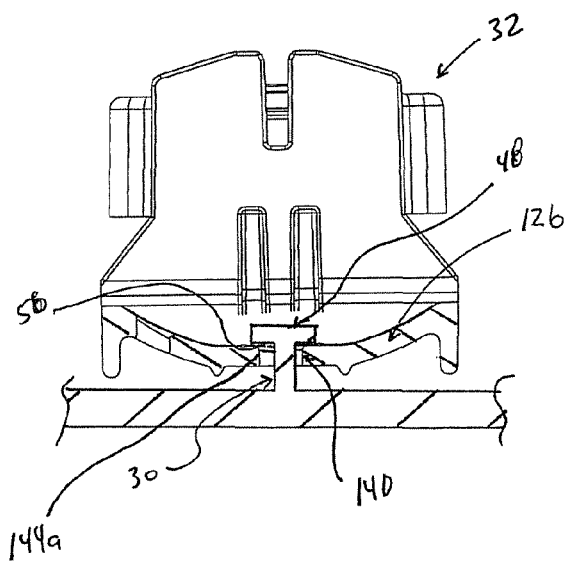

With continued reference between FIGS. 7A and 7B, in some embodiments the end panels 128, 130 locate the corresponding end tab 120, 122 at a spatial location off-set from the platform 126. Regardless, the end panels 128, 130 each from or include a mounting feature 160, 162 configured to facilitate assembly (e.g., static mounting) of the key pin 110 (FIG. 6) as described below. Further, an engagement surface 164, 166 is defined at each of the end panels 128, 130.

Referring to FIG. 6, the key pin 110 includes a pin body 170 terminating at opposing ends 172, 174. The pin body 170 can have a generally cylindrical shape, with the opposing ends 172, 174 each forming a leg 176, 178 or other structure configured to mate with the corresponding slide bar mounting feature 160, 162. The key pin 110 includes one or more shoulders 180 formed as radial projections from an outer diameter of the pin body 170. The number of the shoulders 180 provided with the key pin 110 corresponds with the number of wheel pairs 34, with each shoulder 180 being configured to selectively interface with the corresponding wheel pair 34 as described below.

As a point of reference, FIG. 9 illustrates assembly of the key pin 110 to the slide bar 32. The opposing ends 172, 174 are mounted to respective ones of the end panels 128, 130, for example a snap fit-type interface between the key pin legs 176, 178 (the second leg 178 being hidden in the view of FIG. 9) with a corresponding one of the slide bar mounting features 160, 162. Upon final assembly, the key pin 110 is maintained spatially away from the platform 126 at a distance sufficient to receive the wheel pairs 34 (FIG. 6).

As reflected generally in FIG. 6 and as mentioned above, each of the wheel pairs 34 includes the inner wheel 36 and the outer wheel 38. One embodiment of the inner wheel 36 is shown in greater detail in FIGS. 10A and 10B, and includes or defines a hub 190, a flange 192, and a ring 194. The hub 190 extends from a trailing side 196 to a leading side 198, and has an outer surface 200 defining a relatively uniform maximum outer diameter and optionally forming first and second annular grooves 201a, 201b. The flange 192 is formed as a radial extension from the outer surface 200 at the leading side 198. The ring 194 projects in an axial fashion from the leading side 198.

The inner wheel 36 forms a central passageway 202 that is open at the trailing and leading sides 196, 198. The central passageway 202 is sized to be rotatably received over the key pin body 170 (FIG. 6). Further, the hub 190 defines an inner keyway 204. The inner keyway 204 is open to the central passageway 202, effectively formed as a radial projection from the central passageway 202. The inner keyway 204 is configured to slidably receive a respective one of the key pin shoulders 180 (FIG. 6) when the shoulder 180 is aligned with the inner keyway 204 and as the key pin 110 is translated axially relative to the inner keyway 204 (e.g., the key pin 110 is moved in a direction parallel with inner keyway 204 axis).

Figure 10A:
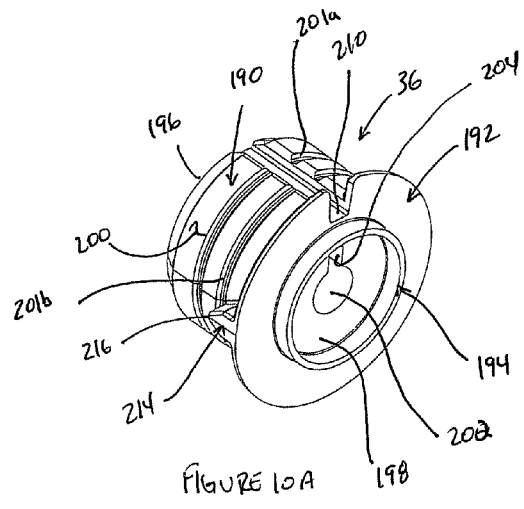
FIGS. 10A and 10B are perspective views of an inner wheel component of the lock mechanism sub-assembly of FIG. 6.
Figure 10B:
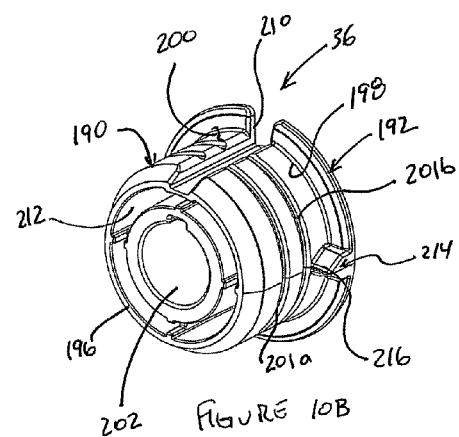
Figure 10C:
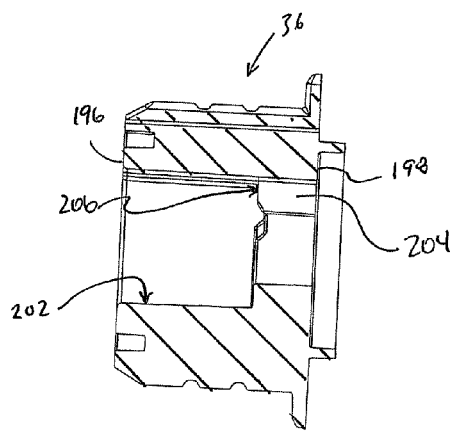
FIG. 10C is a cross-sectional view of the inner wheel of FIG. 10A taken along a line passing through an inner keyway.
Figure 10D:
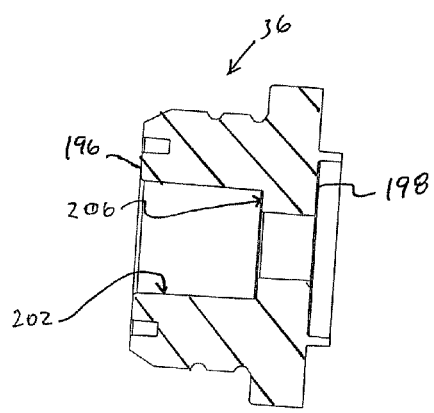
FIG. 10D is a cross-sectional view of the inner wheel of FIG. 10A taken along a line rotated 90 degrees from the view of FIG. 10D.
Figure 10E:
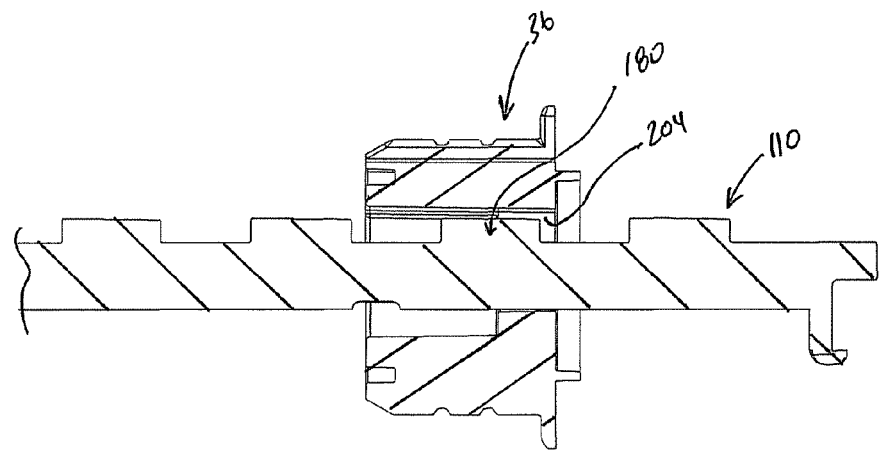
FIGS. 10E and 10F are cross-sectional views illustrating interface between the key pin of FIG. 6 and the inner wheel of FIG. 10A.
Figure 10F:
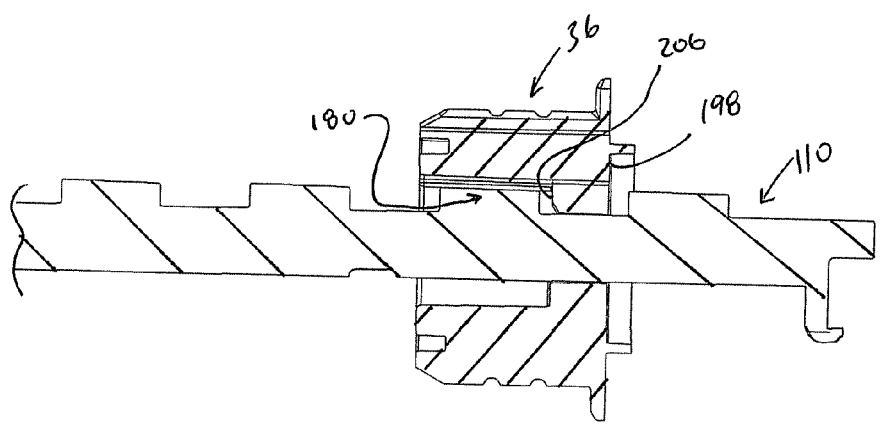

In some constructions, and as shown in FIG. 10C, a diameter of the central passageway 202 is larger at the trailing side 196 than at the leading side 198. Stated otherwise, the hub 190 can form an interior shelf 206, with a diameter of the central passageway 202 being decreased at the interior shelf 206 to the leading side 198. As revealed by a comparison of FIG. 10C (in which the inner keyway 204 is visible) with FIG. 10D (in which the inner keyway 204 is hidden), the inner keyway 204 combines with the central passageway 202 to define a collective diameter sized to permit the key pin 110 (FIG. 6) to freely slide relative to the inner wheel 36 when a predetermined rotational arrangement between the components 36, 110 is provided. More particularly, and as shown in FIG. 10E, when the inner wheel 36 is rotationally arranged relative to the key pin 110 such that the shoulder 180 is aligned with the inner keyway 204, the key pin 110 can slide transversely relative to the inner wheel 36, with the shoulder 180 passing through the inner keyway 204. Conversely, FIG. 10F illustrates an arrangement in which the inner keyway 204 (hidden in the view of FIG. 10F) is not aligned with the shoulder 180; under these circumstances were an attempt made to slide the key pin 110 in a direction of the inner wheel leading side 198 (i.e., rightward relative to the orientation of FIG. 10F), the shoulder 180 would abut the interior shelf 206. Thus, where the inner wheel 36 is held stationary and the shoulder 180 is not aligned with the inner keyway 204, the inner wheel 36 prevents sliding movement of the key pin 110 in at least one direction. Along these same lines, the inner wheel 36 can optionally form minor ramp features on either side of the inner keyway 204 that allow the key pin shoulder 180 to pass into the inner keyway 204 only if the corresponding wheel pair 34 is arranged within the an angular boundary of the correct code character provided on the corresponding outer wheel 38 (described below). Beyond this angular boundary, the key pin shoulder 180 will hit one of the minor ramps and get "kicked out" of the inner keyway 204. Thus, where provided, the minor ramps allow for a slight degree of misalignment of the correct code character during a successful unlock cycle. In other embodiments, the minor ramps are omitted.

Returning to FIGS. 10A and 10B, the inner wheel 36 optionally forms an external keyway 210 as an open slot through the flange 192. The external keyway 210 is sized and shaped to selectively receive a respective one of the front housing section anti-rotation tabs 92 (FIG. 2B), and in some embodiments can extend longitudinally along the outer surface 200 of the hub 190.

The ring 194 is generally configured to interface with either the slide bar 32 (FIG. 6) or an adjacent one of the inner wheels 36 depending upon a location of the inner wheel 36 upon final assembly. In this regard, the inner wheel 36 optionally forms an annular groove 212 at the trailing side 196. The annular groove 212 is sized and shaped in accordance with the ring 194 such that when two of the inner wheels 36 are arranged end-to-end (with the leading side 198 of the first inner wheel 36 facing the trailing side 196 of the second inner wheel 36), the ring 196 of the first inner wheel 36 will nest within the annular groove 212 of the second inner wheel 36. In other embodiments, one or both of the ring 194 and/or the annular groove 212 can be omitted.

The inner wheel 36 provides one or more features for selectively engaging corresponding features provided with the outer wheel 38 (FIG. 6) in manner effectuating a rotation lock between the inner and outer wheels 36, 38. For example, in one embodiment envisioned by the present disclosure, the inner wheel 36 forms or provides one or more prongs 214 (one of which is visible in the views of FIGS. 10A and 10B). The prong(s) 214 is defined as a radial projection from the outer surface 200, extending from the flange 192 in a direction of the trailing end 196. In some embodiments, the prong 214 can have a tapering width, terminating at a tip 216 opposite the flange 192. As described below, the prong(s) 214 is sized and shaped to frictionally engage the outer wheel 38 during use of the lock assembly 12 (FIG. 2).

Figure 11:
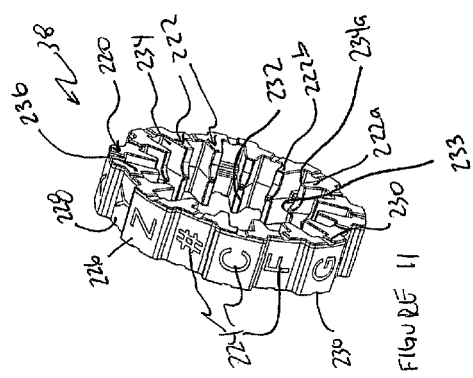
FIG. 11 is a perspective view of an outer wheel component of the lock mechanism sub-assembly of FIG. 6.

One embodiment of the outer wheel 38 is shown in FIG. 11. The outer wheel 38 can generally include or define a wheel body 220 and a plurality of teeth 222 projecting radially inwardly from the wheel body 220 in a spaced-apart fashion. A plurality of code characters 224 are provided on an exterior surface of the wheel body 220. The code characters 224 can assume a variety of forms (letters, numbers, characters, icons, etc.), and each of the code characters provided 224 on the outer wheel 38 differ from a remainder of the code characters 224 on that same outer wheel 38. In one embodiment, the code characters 224 include letters of the English alphabet, but none of the code characters 224 are vowels (thus, when several of the outer wheels 38 are arranged side-by-side, a recognizable English language word cannot be formed). In related embodiments, no two of the code characters 224 provided with a single outer wheel 38 are inverse shapes of one another (e.g., if one of the code characters 224 is the letter "M", none of the remaining code characters 224 will be the letter "W"). The code characters 224 can be provided on the wheel body 220 in a various fashions such as printing, labeling, etc. While the code characters 224 are equidistantly spaced from another about a circumference of the wheel body 220, in some embodiments the wheel body 220 provides alternating raised and recessed zones 226, 228 at which a single one of the code characters 224 is formed. The raised and recessed zones 226, 228 provide the wheel body 220 with a contoured outer surface that facilitates to user manipulation of (i.e., rotating) the outer wheel 38. Finally, the wheel body 220 can form indentations 230, respective ones of which are centered relative to a corresponding one of the code characters 224. Where provided, the indentations 230 assist a user in aligning a desired code character 224 in a desired rotational position as described below.

The teeth 222 extend inwardly about a circumference of the wheel body 220, and are uniformly spaced from one another. Each tooth 222 terminates at a bearing surface 232, with the bearing surfaces 232 being spaced at approximately the same radial distance from a centerline of the outer wheel 38. In some embodiments, one or more or all of the bearing surfaces 232 terminates at a peak 233 at the centerline of the inner diameter of the outer wheel 38. The peak(s) are configured to selectively interface with the inner wheel annular grooves 201a, 201(b) (FIGS. 10A and 10B). Adjacent ones of the teeth 222 combine to define a trough 234. For example, the first tooth 222a and the second tooth 222b identified in FIG. 11 combine define the first trough 234a. The troughs 234 are open at a spacing between the bearing surfaces 232 of the corresponding teeth 222, as well as being longitudinally open at least at a leading edge 236 of the outer wheel 38.

Figure 12A:
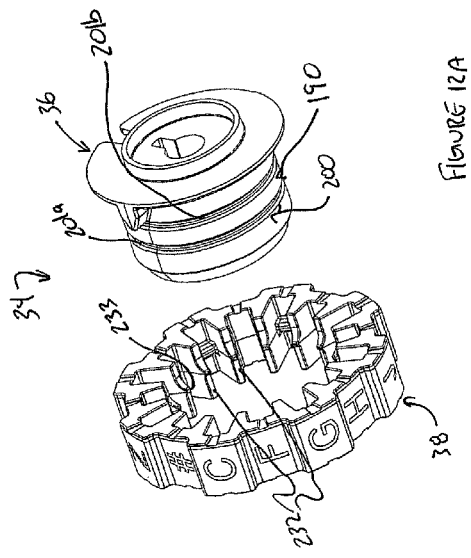
FIGS. 12A-12C are perspective views illustrating interface between the inner wheel of FIG. 10A and the outer wheel of FIG. 11 in forming a wheel pair portion of the lock mechanism sub-assembly of FIG. 6.
Figure 12C:
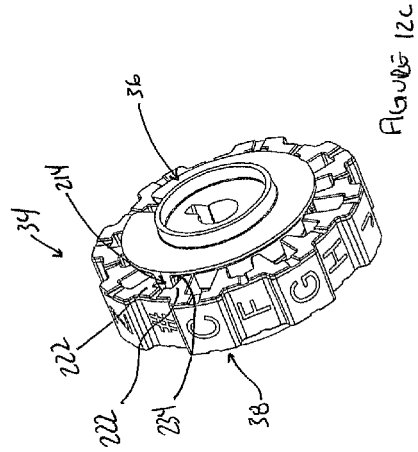
Figure 12B:
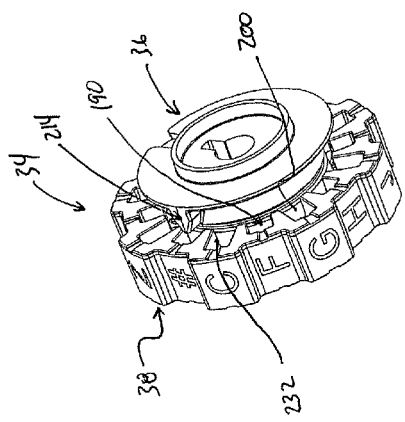

The troughs 234 are sized and shaped to engage a respective one of the inner wheel prongs 24 (FIG. 11A). FIGS. 12A-12C illustrate a relationship between the inner and outer wheels 36, 38 of the wheel pair 34 at various stages. In the view of FIG. 12A, the outer wheel 38 is removed from the inner wheel 36. A diameter collectively defined by the bearing surfaces 232 approximates an outer diameter along the inner wheel hub outer surface 200. To this end, and where provided, the diameter collectively defined by the peaks 233 approximates a diameter of the annular grooves 201a, 201b. With this construction, the hub 190 can be inserted within the outer wheel 38 as shown in FIG. 12B, with one or more of the bearing surfaces 232 slightly contacting the hub outer surface 200. The peaks 203 are located with the first annular groove 201a (hidden in FIG. 12B) and thus aid in positive location of the wheels 36, 38 relative to one another. In the arrangement or state of FIG. 12B, the outer wheel 38 is longitudinally spaced from the inner wheel prongs 214, such that the outer wheel 38 can freely rotate relative to the inner wheel 36 (e.g., while some contact between the bearing surfaces 232 and the hub 190 will occur, a minimal amount of frictional interface is exhibited such that a low moment force applied to the outer wheel 38 by a user will cause the outer wheel 38 to rotate about the hub 190 (under circumstances where the inner wheel 36 is held stationary) including the peaks 233 sliding within the first annular groove 201a). That is to say, FIG. 12B reflects a connected but rotationally uncoupled state of the wheel pair 34. With further longitudinal insertion of the inner wheel 36 into the outer wheel 38 (e.g., generally leftward relative to the orientation of FIG. 12B), the inner wheel prong 214 is forced into one of the troughs 234 establishes a coupling with the corresponding adjacent teeth 222 as shown in FIG. 12C. Further, where provided, the peaks 233 (FIG. 12A) shift into the second annular groove 201b (FIG. 12A) to maintain engagement between the wheels 36, 38. In the rotationally coupled arrangement or state of FIG. 12C, a moment force applied to the outer wheel 38 is transferred to the inner wheel 36 (at the prong 214/teeth 222 interface), such that inner and outer wheels 36, 38 will rotate in tandem. Stated otherwise, in the coupled state of FIG. 12C, the wheel pair 34 is effectively a singular component.

Figure 13A:
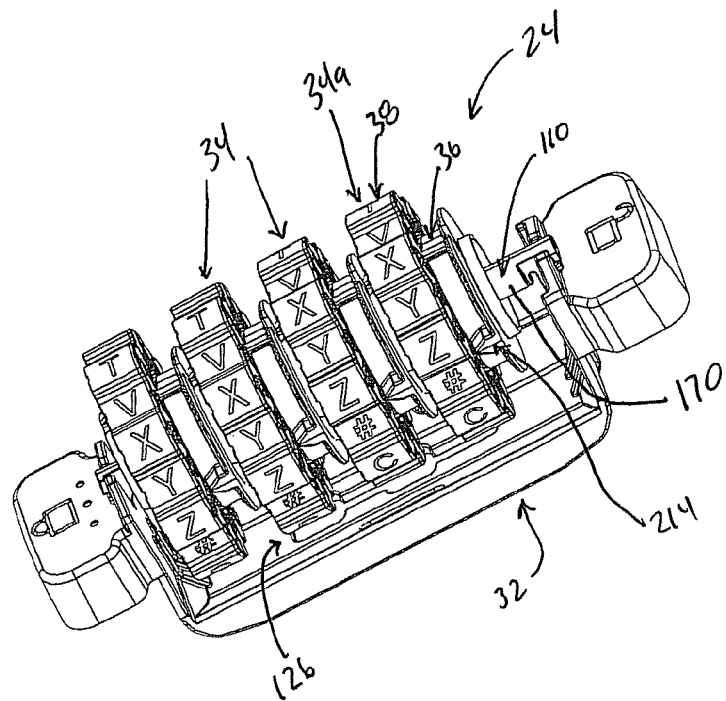
FIG. 13A is a perspective view of the lock mechanism sub-assembly of FIG. 6 upon final assembly and illustrating a combination unset state.

Final construction of the lock mechanism sub-assembly 24 is shown in FIG. 13A. Prior to mounting the key pin 110 to the slide bar 32 as described above (FIG. 9), the wheel pairs 34 are loaded over the pin body 170, with the pin body 170 thus serving as a common axis of rotation of the wheel pairs 34. Following mounting of the key pin 110 to the slide bar 32, the wheel pairs 34 are spaced from the platform 126 by a distance sufficient to permit rotation of the outer wheels 38 about the axis, as well as lateral movement or sliding of the platform 126 relative to the outer wheels 38.

Explanations of the combination unset and set states, and the correctly entered code and incorrectly entered code arrangements, can be made with reference to FIGS. 13A-16B. The combination unset and set states relate to whether or not a particular combination code has been assigned or "entered" into the lock assembly 12, or more particularly whether or not the corresponding inner and outer wheels 36, 38 of each of the wheel pairs 34 have been coupled to one another. The correctly entered code and incorrectly entered code arrangements relate to whether or not an code inputted by a user (e.g., in some embodiments, the code characters collectively displayed by the outer wheels 38) corresponds to the combination assigned to the lock assembly 12 thus permitting movement or transitioning of the lock assembly between the locked and unlocked positions, and in particular (with the but one acceptable embodiment envisioned by the present disclosure in FIGS. 13A-16B) whether or not the inner keyways 204 are aligned with the corresponding key pin shoulders 180. From this explanation, it will be understood that when the lock assembly 12 is in the combination unset state, the correctly or incorrectly entered code is meaningless; until the combination has been set into the lock assembly 12 (i.e., the combination set state), a "correct" or "incorrect" code does not exist.

In the combination unset state of FIG. 13A, the inner and outer wheels 36, 38 of each of the wheel pairs 34 are rotationally uncoupled (i.e., relative to the first wheel pair 34a identified in FIG. 13A, the inner wheel prong(s) 214 is longitudinally displaced from the corresponding outer wheel 38). Further, and as shown in FIG. 13B, the wheel pairs 34 are associated with a respective one of the key pin shoulders 180, with each of the shoulders 180 being aligned within the corresponding inner keyway 204 (referenced generally).

Figure 13B:
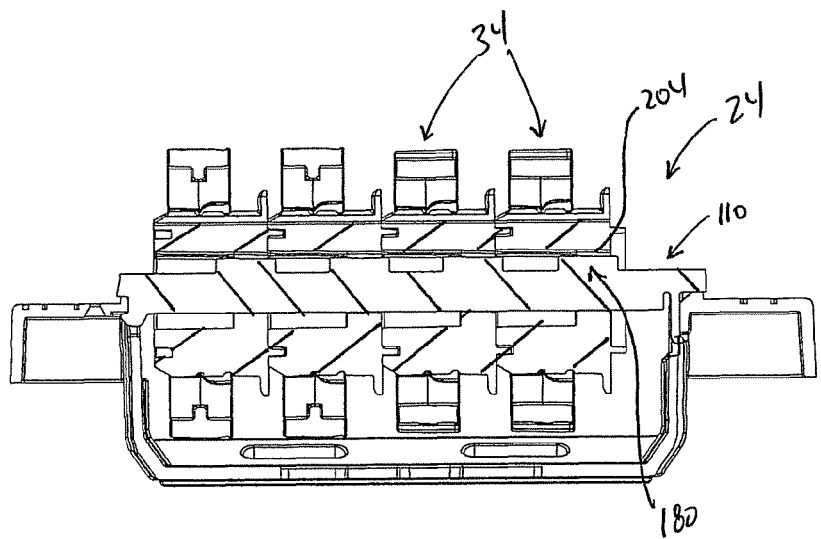
FIG. 13B is a cross-sectional view of the lock mechanism sub-assembly of FIG. 13A.
Figure 14A:
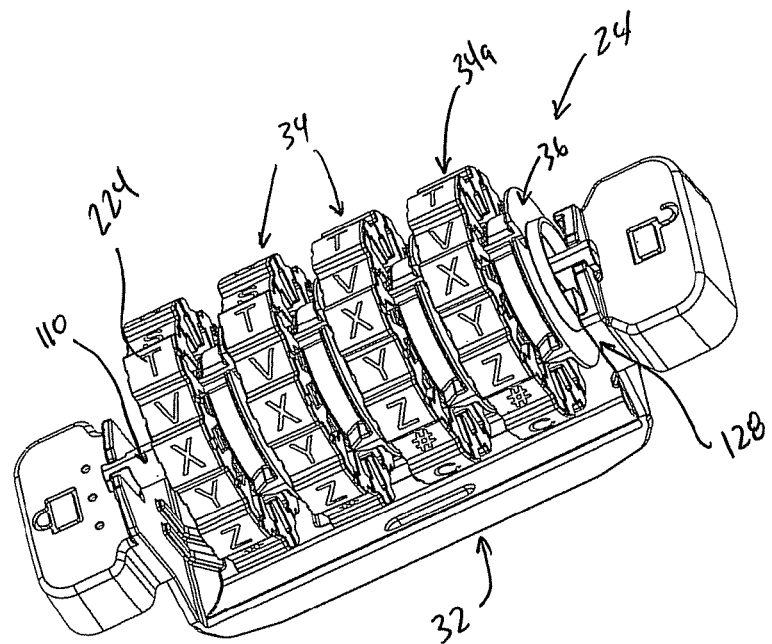
FIG. 14A is a perspective view of the lock mechanism sub-assembly of FIG. 6 and illustrating initial transitioning from the combination unset state to the combination set state.
Figure 14B:
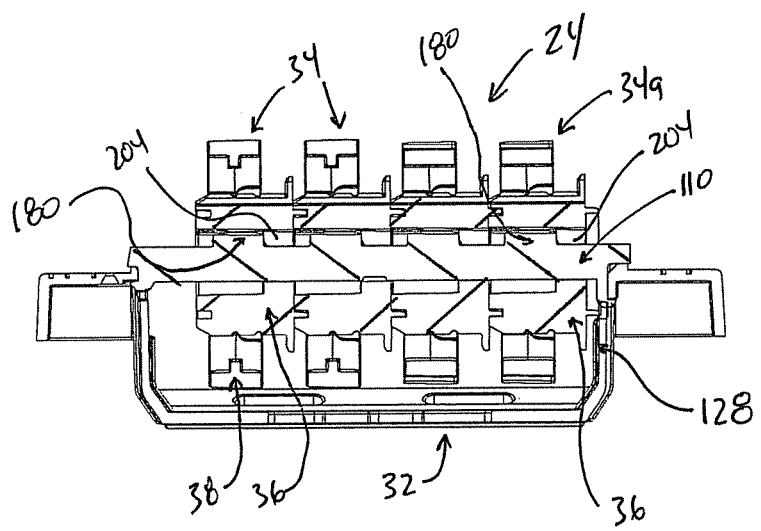
FIG. 14B is a cross-sectional view of the lock mechanism sub-assembly of FIG. 14A.

The lock mechanism sub-assembly 24 can be transitioned to combination set state from the initial arrangement of FIGS. 13A and 13B. For example, in FIGS. 14A and 14B, the slide bar 32 has been moved laterally relative to the wheel pairs 34 (i.e., the slide bar 32 has been moved in a leftward direction in transitioning from the arrangement of FIG. 13B to the arrangement of FIG. 14B). The first end panel 128 of the slide bar 32 is brought into slight contact with the inner wheel 36 of the first wheel pair 34a. The key pin 110 moves with lateral movement of the slide bar 32, with FIG. 14B reflecting that the shoulders 180 are outside of the corresponding inner keyway 204, and are adjacent the corresponding interior shelf 206. In the arrangement of FIGS. 14A and 14B, the inner and outer wheels 36, 38 of each of the wheel pairs 34 remain rotationally uncoupled, such that the lock mechanism sub-assembly 24 continues to be in the combination unset state. Thus, the outer wheel 38 can freely rotate relative to its corresponding inner wheel 36, for example to allow a user to rotationally arrange each of the outer wheels 38 relative to the corresponding inner wheel 36 such that a desired code character 224 is visible at the housing 22 (FIG. 2A).

Once the outer wheels 38 are rotationally arranged as desired (e.g., a desired code combination is collectively displayed by the outer wheels 38), with further transverse movement of the slide bar 32 relative to at least the outer wheels 38 from the arrangement of FIGS. 14A and 14B (e.g., in same leftward direction as transitioning from FIG. 13A to FIG. 14A), the slide bar 32 exerts a transverse force on to the inner wheel 36 of the first wheel pair 34a. As illustrated, adjacent ones of the inner wheels 36 abut one another such that the transverse force on the first wheel pair inner wheel 36 is transferred to each of the remaining inner wheels 36. Under circumstances where the outer wheels 38 are held stationary, each of the inner wheels 36 is thus caused to move transversely relative to the corresponding outer wheel 38, resulting in the combination set state of FIGS. 15A and 15B in which the inner wheel 36 of each of the wheel pairs 34 is rotationally coupled to the corresponding outer wheel 38.

Figure 15A:
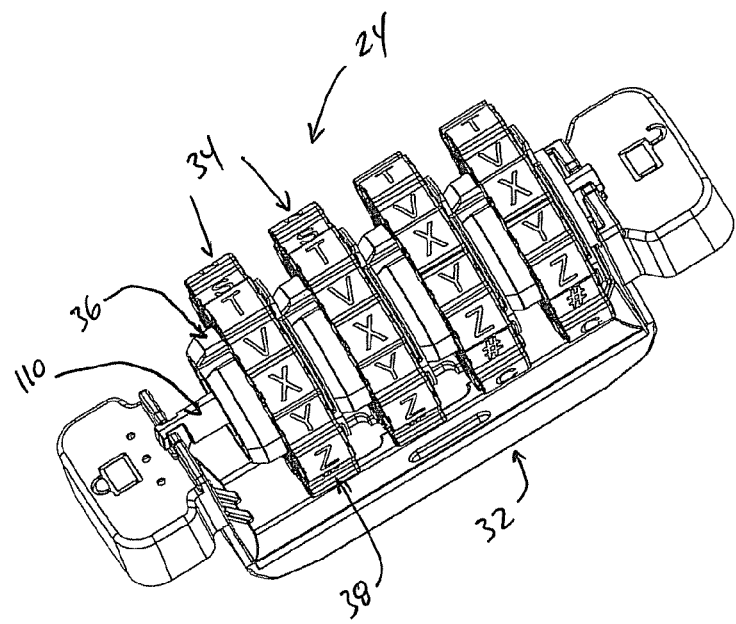
FIG. 15A is a perspective view of the lock mechanism sub-assembly of FIG. 6 and illustrating a combination set state and a correct code arrangement.
Figure 15B:
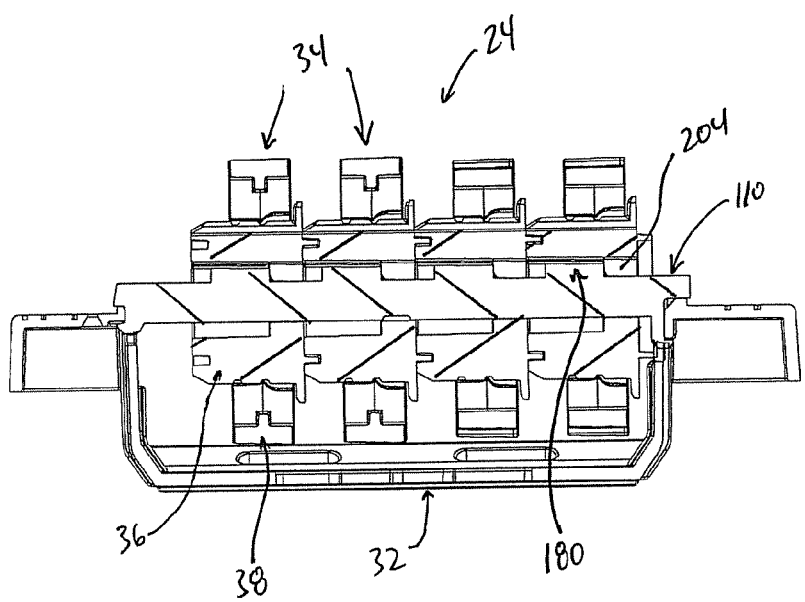
FIG. 15B is a perspective view of the lock mechanism sub-assembly of FIG. 15A.
Figure 16A:
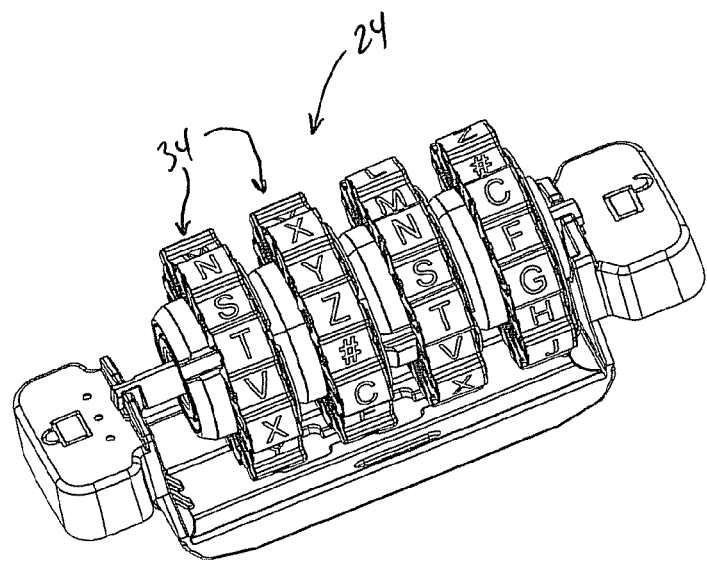
FIG. 16A is a perspective view of the lock mechanism sub-assembly of FIG. 6 and illustrating an incorrect code arrangement.
Figure 16B:
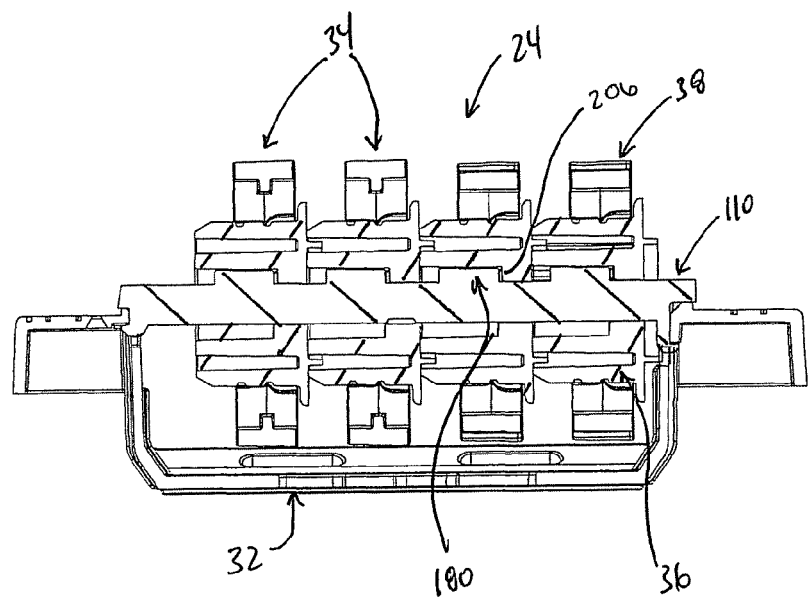
FIG. 16B is a cross-sectional view of the lock mechanism sub-assembly of FIG. 16A.

With specific reference to FIG. 15B, so long as the wheel pairs 34 are rotationally positioned relative to the key pin 110 such that each of the shoulders 180 is aligned with the corresponding inner keyway 204, the key pin 110, and thus the slide bar 32, can be moved transversely in the opposite direction relative to the wheel pairs 34 (i.e., rightward relative to the orientation of FIG. 15B). This represents the correctly entered code arrangement of the lock assembly 12. However, and as shown in FIGS. 16A and 16B, when one or more of the wheel pairs 34 are rotated such that the inner keyway 204 (hidden in FIGS. 16A and 16B) is no longer aligned with the corresponding key pin shoulder 180 (e.g., the incorrectly entered code arrangement), the wheel pairs 34, and in particular the inner wheel interior shelves 206, prevent the key pin 110, and thus the slide bar 32, from moving in at least one direction (rightward relative to the orientation of FIG. 16B) relative to the wheel pairs 34. Thus, FIGS. 16A and 16B reflect the combination set state of the lock mechanism sub-assembly 24, as well as the incorrectly entered code arrangement.

Final construction of the lock assembly 12 is shown in FIGS. 17A and 17B. As a point of reference, the wheel pairs 34 are in the combination unset state. The lock mechanism sub-assembly 24 is disposed within the housing 22. More particularly, the slide bar platform 126 bears against the inner face 66 of the rear housing section bottom wall 60, with respective ones of the guide pins 74-74c (two of which are visible in FIG. 17B) slidably disposed within a corresponding one of the platform guide slots 152a-152c (two of which are visible in FIG. 17B). Each of the outer wheels 38 are disposed within a respective one of the front housing section slots 86 such that each of the outer wheels 38 can rotate relative to the housing 22 (about the common axis of rotation defined by the key pin 110) but are overtly limited from transverse movement (i.e., the front housing section 28 prevents the outer wheels 38 from moving transversely with transverse movement of the slide bar 32/key pin 110, and further serves to resist a transverse direction force applied by the key pin 110 on to the outer wheel 38 (when the outer wheel is coupled to the corresponding inner wheel 36)).

With this construction, the lock assembly 12 can be transitioned between the locked position and the unlocked position, with the positions being in general reference to a relationship of the slide bar 32, and in particular the slide bar capture slot 180, relative to the rear housing section aperture 64. FIG. 17B reflects the unlocked position. The slide bar 32 is positioned a maximum distance leftward relative to the housing 22, bringing the clearance segments 142a, 142b of the capture slot 180 into alignment with the aperture 64. In the locked position of FIG. 17C, the slide bar 32 has translated rightward relative to the housing 22, moving the capture slot clearance segments 142a, 142b out of alignment with the aperture 64 (such that the capture slot locking tabs 144a, 144b. As a point of reference, FIG. 17C illustrates the wheel pairs 34 in the combination set state, the key pin 110/wheel pairs 34 in the incorrectly entered code arrangement, and the slide bar 32 in the locked position.

To summarize the various operational modes of FIGS. 13A-17C, the lock assembly 12 effectively provides three discrete operational parameters. First, the inner and outer wheels 36, 38 of each of the wheel pairs 34 are either uncoupled or coupled to one another (with the uncoupled relationship also referred to as the combination unset state, and the coupled relationship also referred to as the combination set state). Second, the inner keyway 204 of each of the inner wheels 36 is either aligned or unaligned with the corresponding key pin shoulder 180 (with the aligned relationship also referred to as the correctly entered code arrangement, and the unaligned relationship also referred to as the incorrectly entered code arrangement). Third, the slide bar 32 is transversely arranged relative to the aperture 64 between a first transverse position and a second transverse position, with the first transverse position also referred to as the unlocked position, and the second transverse position also referred to as the locked position. The discrete parameters are interrelated to one another. For example, when the lock assembly 12 is in the combination unset state, the outer wheels 38 freely move relative to the corresponding inner wheels 36 such that a correct or incorrect combination entry arrangement is effectively a subset of the combination set state. Once in the combination set state, the correctly or incorrectly entered code arrangement dictates whether or not the lock assembly 12 (and in particular the slide bar 32) is free to transition between the locked and unlocked positions. In the incorrectly entered code arrangement, the slide bar 32 is prevented from transitioning from the locked position to the unlocked position; conversely, in the correctly entered code arrangement, the slide bar 32 is free to translate from the locked position to the unlocked position.

Figure 18:
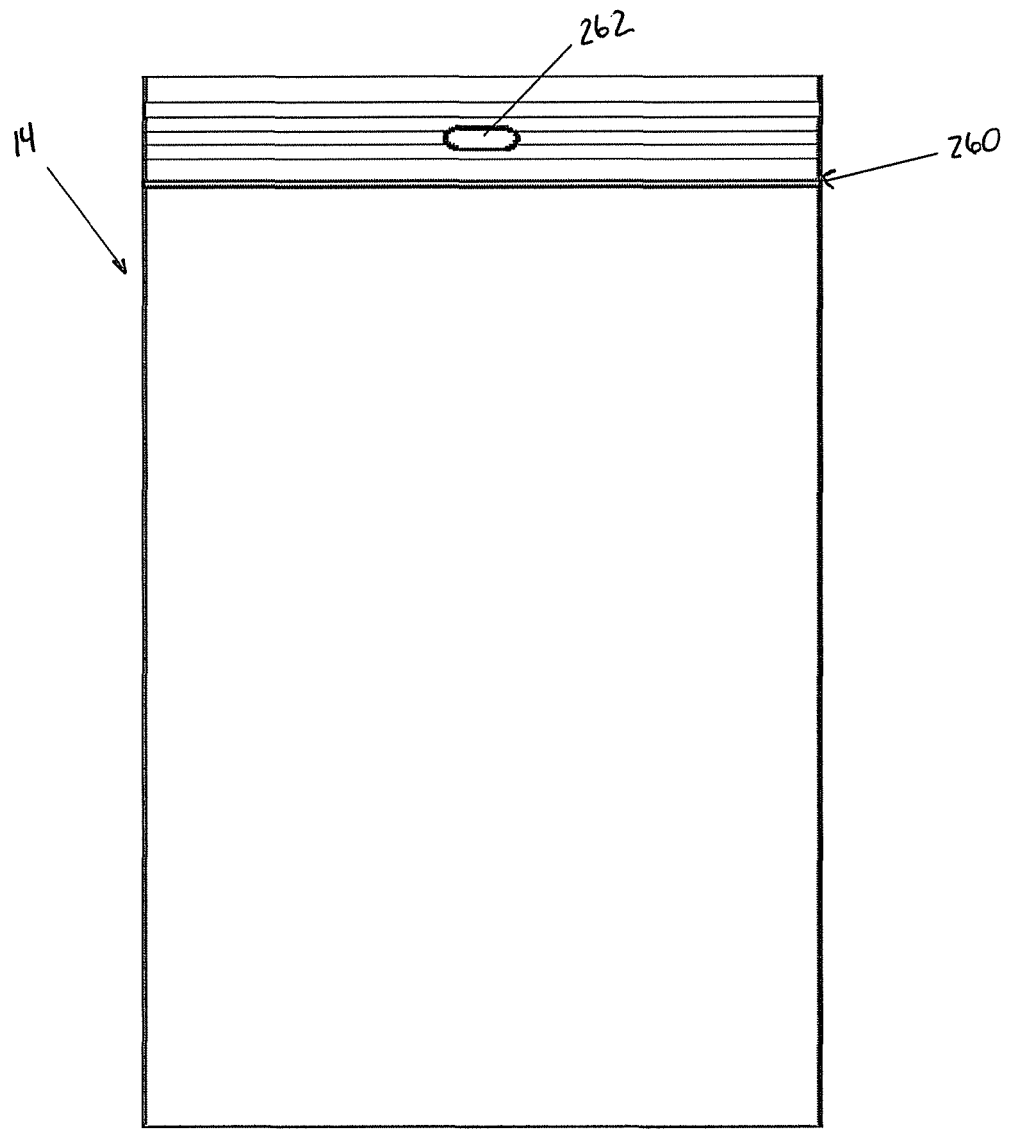
FIG. 18 is a simplified front plan view of an optional overbag component of the system of FIG. 1.
Figure 19:
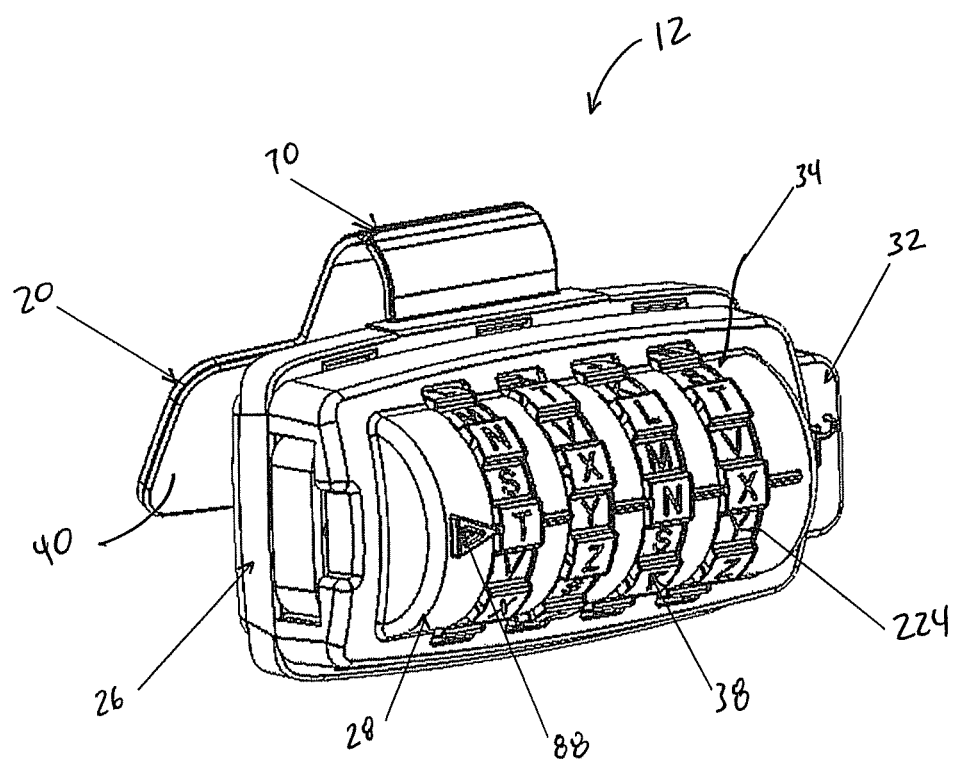
FIG. 19 is a perspective view of the lock assembly component of the system of FIG. 1, illustrating a barrel wheel character selection interface.

Returning to FIG. 1, the optional overbag 14 can assume various forms appropriate for temporarily containing, in a secure manner, patient-related articles of interest. FIG. 18 shows one embodiment of the overbag 14 component of the mechanical barrier recipient verification system 10 (FIG. 1) in greater detail. The overbag 14 has an interior portion sealed by a zipper closure 260 or similar device that helps to contain any materials from spilling during transport of the overbag 14. The contents of the overbag 14 are ultimately secured by attaching the lock assembly 12 (FIG. 1) at a registration hole 262 formed in the overbag 14 as described below.

FIG. 1 shows the optional unique identifier label set 16 used in conjunction with the mechanical barrier recipient verification system 10. The unique identifier label set 16 consists of a unique identifier patient label 270 and a unique identifier specimen label 272. In some embodiments, the unique identifier patient label 270 and the unique identifier specimen label 272 are provided in a format conducive for the purpose of labeling, for example, a patient wristband (not shown) and a patient specimen collection test tube (not shown) to be used in laboratory testing, respectively. In this configuration, the unique identifier patient label 270 is attached via a perforation 273 to the unique identifier specimen label 272 to allow the two labels to remain positively associated until the moment that the specimen label 272 is attached to the specimen collection test tube (not shown) desired to be associated with the receiving patient. This is but one possible configuration envisioned by the present disclosure, and other formats are equally acceptable. For example, additional unique identifier specimen labels 272 could be included for various purposes. Further, the "specimen" label 272 can be configured or used for labeling patient-related articles other than a specimen tube or other type of specimen container. Thus, the specimen label 272 is more broadly viewed as a patient article label. Regardless, the labels 270, 272 display a unique identification code that can be correlated with a recipient (e.g., patient) assigned to the label set 16. The code can be displayed in differing formats (e.g., human readable, machine readable, etc.) on the labels 270, 272, but represents identical information. For example, the patient label 270 can display the identification code as a unique identifier human readable code 274, and the specimen label 272 can display the code as a unique identifier machine readable code 276.

In addition to the human readable code 274, the patient label 270 can also display the matching machine readable code 276. The patient label 270 can also include code alignment indicia 278, which matches the similar code alignment indicia 88 on the lock assembly 12 as seen in FIG. 2A. The optional alignment indicia 278 can assume various forms (e.g., the triangular representation shown) and generally serves to provide a visual clue as to where the code 274 "starts" (e.g., where the code 274 consists of four letters, the indicia 278 readily informs the viewer as to which letter in the code 274 is "first" and then to employ this so-identified "first" letter as the "first" letter when operating the lock assembly 12 as described below). The code represented by the unique identifier machine readable code 276 on the specimen label 272 is the same as that represented by the unique identifier human readable code 274 and can be formatted as any acceptable barcode format, including either linear or 2D barcode formats or both. In some embodiments, the ability to generate additional matching labels could be provided by scanning the machine readable code 276 and printing the desired number of extra labels using well known scanning and printing technologies. Regardless, the unique identifier label set 16 can be constructed using simple pressure sensitive adhesive label sheet materials well known to those skilled in the art.

In some embodiments, the patient label 270 and the specimen label 272 are integrally formed on a common label layer (e.g., adhesive backed, label stock material) that in turn is carried by a common release liner 280. The cut line 273 otherwise serving to demarcate the patient label 270 from the specimen label 272 is formed only through the label layer and does not pass through the release liner 280. A secondary cut line (e.g., line of perforations) 282 is imparted through only the liner 280 at a location off-set from the specimen label 272 (and otherwise "under" the patient label 270). During use, the patient label 270 can be partially removed or peeled from the release liner 280, starting from an end 284 of the patient label 270 opposite the specimen label 272. Once the region of separation between the patient label 270 and the release liner 280 has progressed slightly beyond the secondary cut line 282, the exposed segment of the release liner 280 can be separated from a remainder of the release liner 280, with the adhesive side of the corresponding portion of the patient label 270 now being exposed and available for attachment to a separate article (e.g., a patient wristband). A portion of the release liner 280 opposite the cut line 282 remains connected to the patient label 272, such that the specimen label 272 is effectively connected to the separate article with the adhesive side of the specimen label 272 remaining "covered" or protected by the release liner 280. When application of the specimen label 272 to a specimen container is desired, the specimen label 272 is simply peeled from the release liner 280 and separated from the patient label 270 at the cut line 273.

While the unique code (e.g., the human readable code 274) has been described as being provided with the label set 16, systems of the present disclosure can generate and/or deliver the unique code to a user in other fashions. For example, the unique code can be displayed on an electronic display screen (e.g., computer, tablet, etc.), a printed or hand-written paper or other document, etc. Thus, while the unique code is part of the systems 10 of the present disclosure, the label set 16 in and of itself is optional.

With the above in mind, and with cross-reference between FIGS. 1-2B and 19, overbag mounting-related features of the lock assembly 12 include the optional back plate unit 20, the rear housing section 26, and the slide bar 32. As described in greater detail below, the slide bar 32 also serves as a locking-related component of the lock assembly 12, and is slidable relative to the rear housing section 26 between the unlocked position and the locked position (e.g., FIG. 17C) in setting a combination to the lock assembly 12. Once the combination is set, the slide bar 32 is slidable between the locked position and the unlocked position when locking or unlocking the lock assembly 12. The back plate unit 20 is movably connected to the rear housing section 26 by the connector body 70, such that the back plate 40 can be pivoted or otherwise moved relative to the rear housing section 26 between an open configuration and a closed configuration. As implicated by the view of FIG. 19 (that otherwise reflects the back plate 40 arranged between the fully open configuration and the fully closed configuration), the back plate 40 is readily movable relative the rear housing section 26, constrained only by the connector body 70. In the closed configuration, the post 30 or other mating feature provided with the back plate unit 20 is inserted within the rear housing section 26 and interfaces with the slide bar 32 (in the unlocked position, the slide bar 32 permits insertion of the post 30 or other mating feature), thereby capturing an item (e.g., the overbag 14) disposed between the back plate 40 and the rear housing section 26. Further, with the back plate 40 in the closed configuration, the slide bar 32 can be transitioned from the unlocked position to the locked position, thereby capturing the back plate 40 in the closed configuration. Thus, mounting-related features of the lock assembly 12 provide two related actions; movement of the back plate 40 between open and closed configurations, and transitioning of the slide bar 32 between the unlocked and locked positions. When the slide bar 32 is in the unlocked position, the back plate 40 can be moved to (or from) the closed configuration; when the back plate 40 is in the closed configuration and the slide bar 32 is in the locked position, the slide bar 32 prevents movement of the back plate 40 from the closed configuration. Movement of the slide bar 32 from the locked position can be prevented by transitioning the lock assembly 12 to the incorrectly entered code arrangement. In this regard, the lock assembly 12 can be in the locked or unlocked position independent of the open or closed configuration of the back plate 40; however, once the back plate 40 is in the closed configuration, the slide bar 32 is in the locked position, and the lock assembly 12 is in the incorrectly entered code arrangement, the slide bar 32 cannot be transitioned back to the unlocked position (and thus the back plate 40 cannot be moved to the open configuration) without first transitioning the lock assembly 12 to the correctly entered code arrangement.

As a point of reference, the rear housing section 26 is further assembled to the front housing section 28, with the housing sections 26, 28 serving to maintain the lock mechanism sub-assembly 24 or other components of the lock assembly 12. For example, visible in the front housing section 28 are a plurality of the outer wheels 38 which are decorated with the code characters 224 (e.g., in FIG. 19, the code characters 224 are letters of the English alphabet). The outer wheels 38 are used to enter the unique identifier code inline with the code alignment indicia 88 as explained below.

Figure 20:
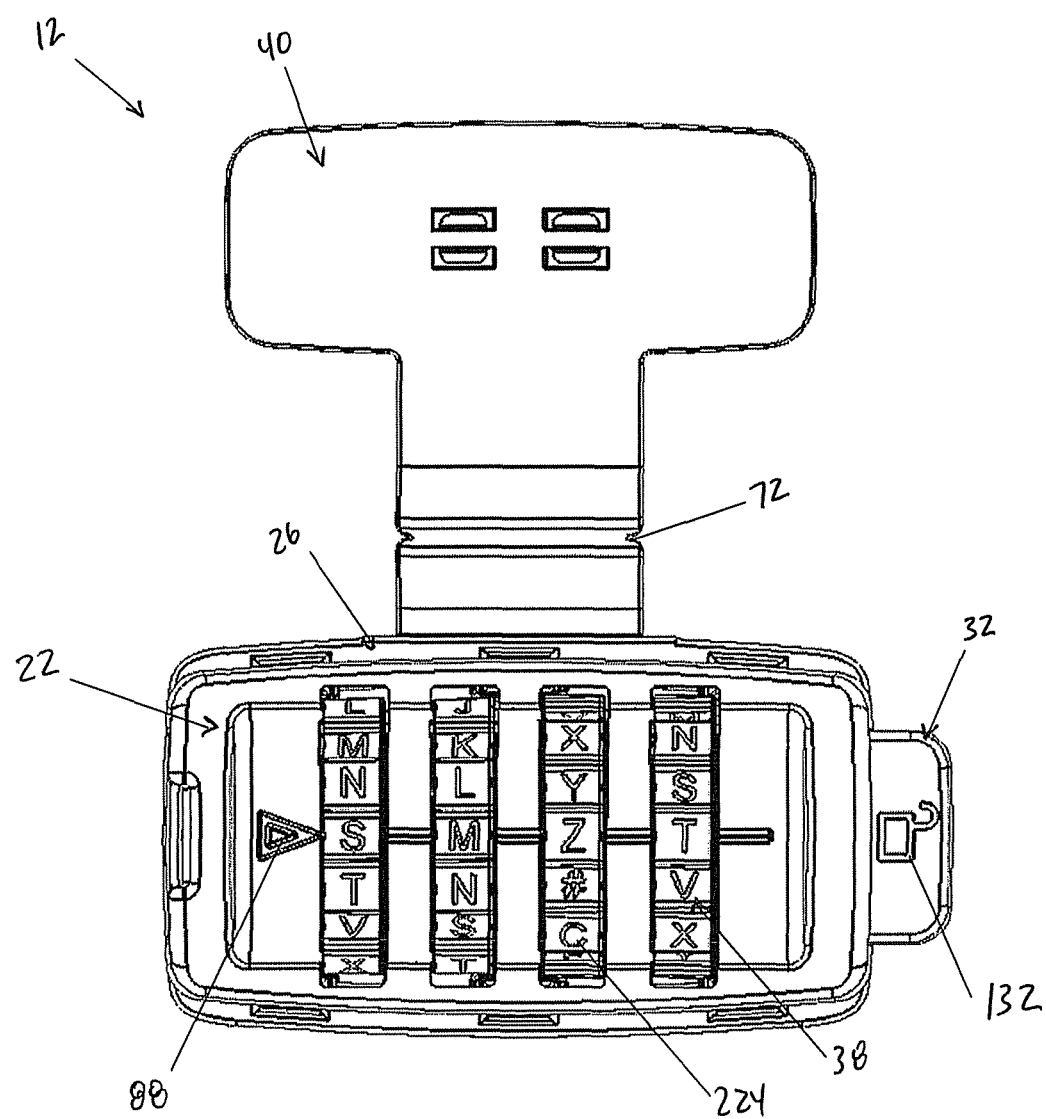
FIG. 20 is a front view of the lock assembly of FIG. 1 in an open arrangement and unlocked position.

Mounting-related features of the lock assembly 12 are better illustrated in FIG. 20 that otherwise provides a front detail view of the back plate 40 in the open configuration (and the lock assembly 12 in the unlocked position). In the open configuration, the back plate 40 is extended away from the main portion of the rear housing section 26, with the hinge 72 in an unflexed state. As shown, the slide bar 32 is partially extended from the housing 22, with the unlocked icon 132 formed on the slide bar 32 being visible. This represents the beginning state for the lock assembly 12 when in use, and includes the lock assembly 12 in the combination unset state. The user would then manipulate the outer wheels 38 to align the code characters 224 in an order corresponding to the unique identifier human readable code 274 (FIG. 1) from the unique identifier label set 16 (FIG. 1). The code characters 224 are aligned with the alignment feature 88 before proceeding to permanently set that specific code to the lock assembly 12.

Figure 21:
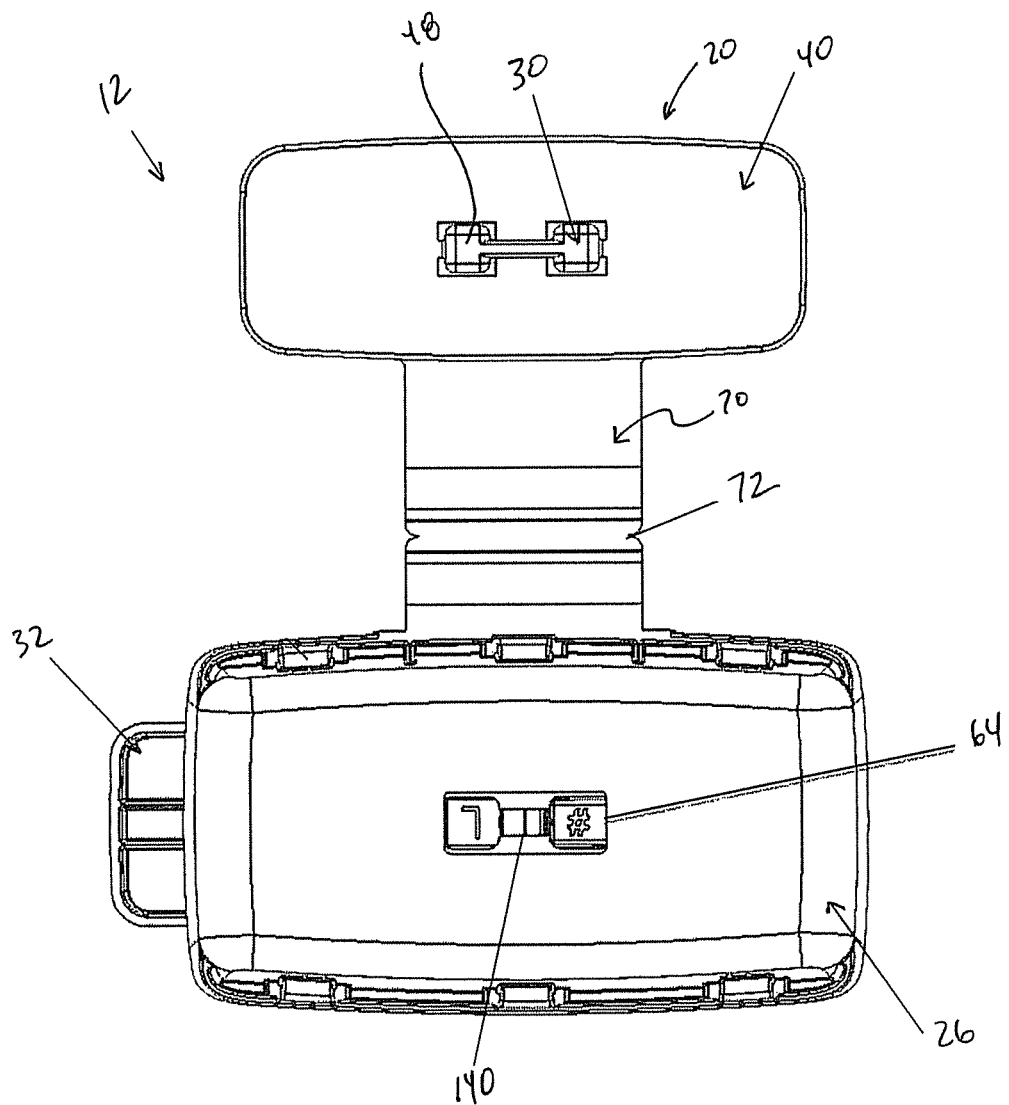
FIG. 21 is a rear view of the lock assembly of FIG. 20.

FIG. 21 shows the back view of the back plate 40 in the open configuration (and the lock assembly 12 in the unlocked position). To facilitate subsequent mounting of the overbag 14 (FIG. 1) between the back plate 40 and the rear housing section 26 in the closed configuration, the back plate unit 20 forms or carries the post 30 and the rear housing section 26 forms the aperture or clearance slot 64 sized and shaped to slidably receive the post 30. When attaching the lock assembly 12 to the overbag 14, the connector body 70 is flexed at the hinge 72 to allow the post 30 to enter the rear housing section 26 through the clearance aperture 64. When the slide bar 32 is in the unlocked position, the capture slot 140 carried by the slide bar 32 is positioned so as to allow the post 30 to travel into the capture slot 140. When the lock assembly 12 is in the combination set state and attached to the overbag 14, the slide bar 32 is moved from the unlocked position to the locked position, thus creating an interference between the capture slot 140 and the head 48 of the post 42 (also shown in FIG. 8B), thereby establishing fixed attachment of the back plate 40 in the closed configuration.

Figure 22:
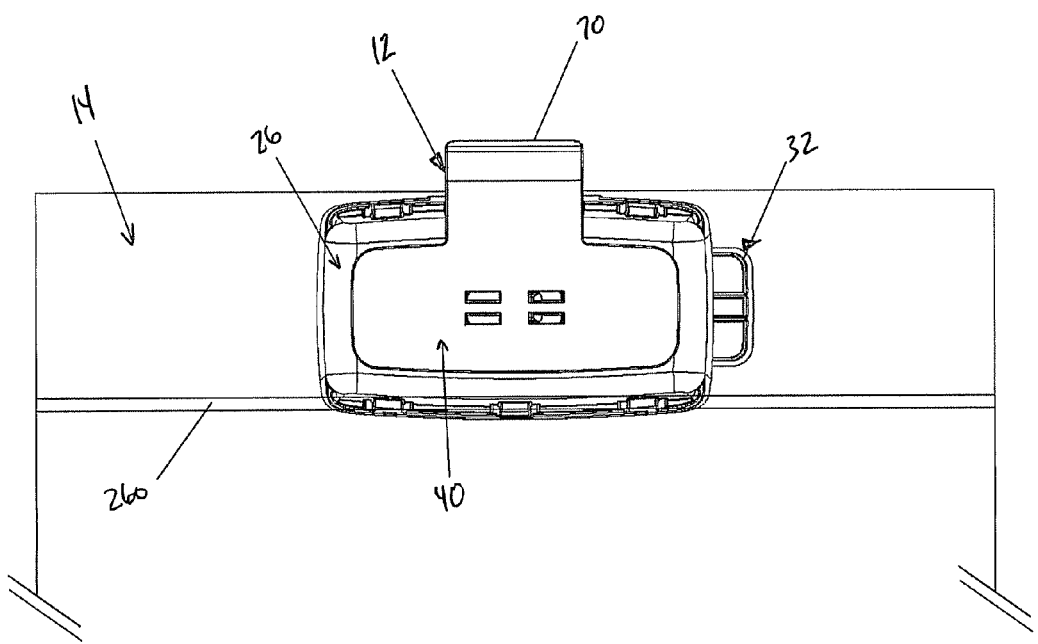
FIG. 22 is a rear view of a portion of the system of FIG. 1, illustrating the lock assembly attached to the overbag.

FIG. 22 depicts the back view of the lock assembly 12 when attached to the overbag 14, including the back plate 40 moved to the closed configuration (and the slide bar 32 in the locked position). The lock assembly 12 is positioned above the zipper closure 260 on the overbag 14. This allows the overbag 14 to remain sealed when the lock assembly 12 is attached. The connection of the back plate 40 via the connector body 70 ensures that the lock assembly 12 can only be applied in one orientation, and also prevents the lock assembly 12 from rotating about the post 30 (FIG. 2A) and within the overbag registration hole 262 (FIG. 18) to maintain maximum blockage of the overbag 14 aperture.

Figure 23:
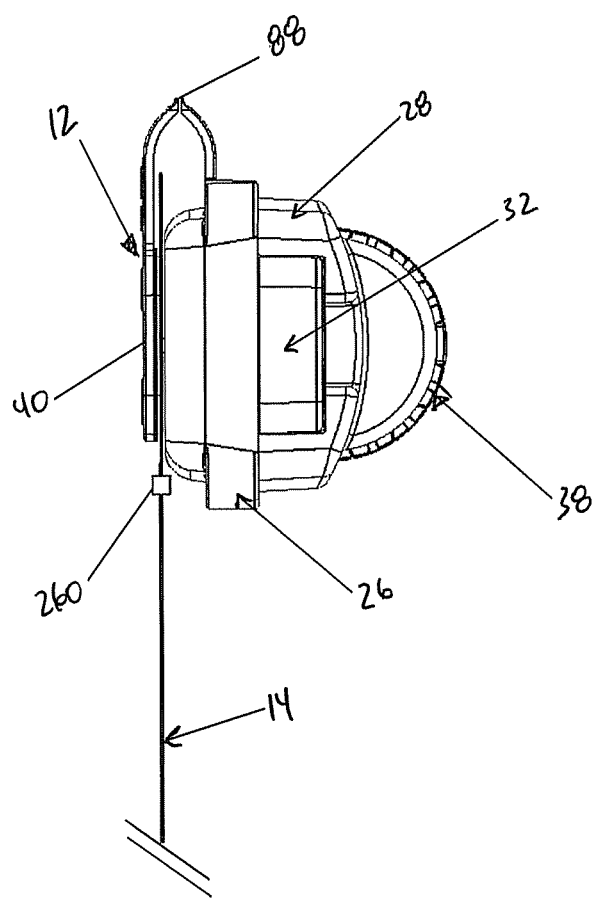
FIG. 23 is a side view of a portion of the system of FIG. 22.

FIG. 23 shows a side view of the lock assembly 12 when attached to the overbag 14, including the back plate 40 in the closed configuration (and the slide bar 32 in the locked position). The overbag 14 is held captive between the back plate 40 and the rear housing section 26 to prevent access to the interior of the overbag 14 until the lock assembly 12 is properly decoded and transitioned to the unlocked position as described below (e.g., by referring to the unique identifier patient label 220 (FIG. 1) and entering the unique identifier human readable code 274 (FIG. 1) by manipulating the outer wheels 38). If the code is correct (i.e., the lock assembly 12 is successfully transitioned to the correctly entered code arrangement), the user will be able to move the slide bar 32 from the locked position to the unlocked position (signified by the visibility of one of the locked icon 134 and the unlocked icon 132, respectively, as best seen in FIG. 2A).

Figure 24:
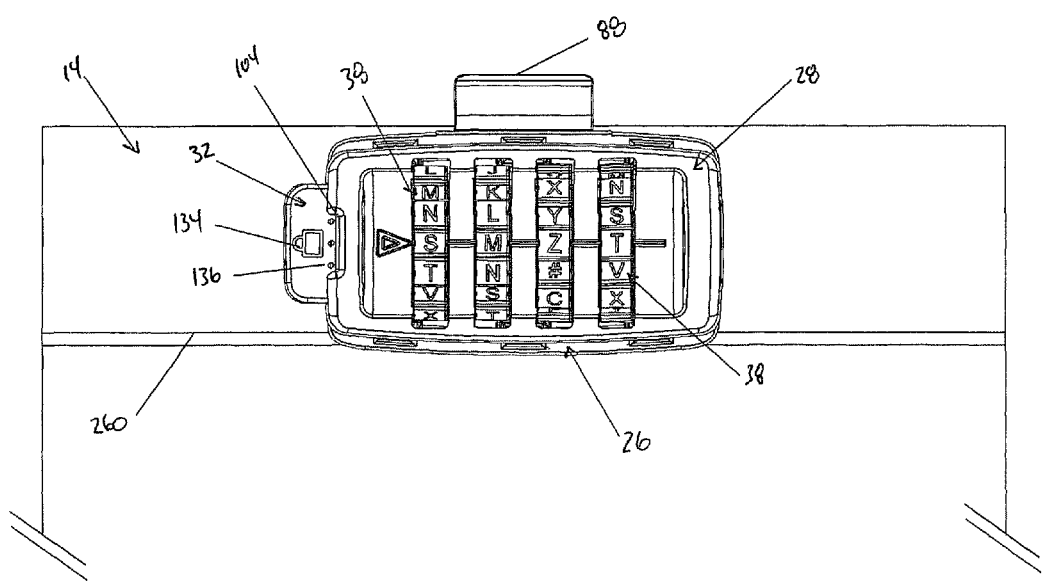
FIG. 24 is a front view of a portion of the system of FIG. 22.

As mentioned above, the slide bar 32 is slidable relative to the rear housing section 26 (and the front housing section 28), and serves to capture the back plate 40 relative to the rear housing section 26 when transitioned from the unlocked position to the locked position, and release the back plate 40 relative to the rear housing section 26 when transitioned from the locked position to the unlocked position. As a point of clarification, movement of the slide bar 32 is employed during two discrete stages of operation. First, during a combination setting stage, the slide bar 32 is transitioned between the unlocked position (or a position in close proximity to the unlocked position) and the locked position. As alluded to above, the unset/set states of the lock assembly 12 relate to establishment of a combination for the lock assembly 12, and are generally independent of the lock/unlocked positions (e.g., in the unlocked position, the lock assembly 12 can be in either the unset state or the set state). Second, during a locking-unlocking stage, the slide bar 32 is transitioned between the unlocked position and the locked position to lock or unlock the lock assembly 12. Various internal locking-related components of the lock assembly 12 interface with the slide bar 32 in connection with these sliding movements as described below. In more general terms, FIG. 20 reflects the slide bar 32 in the unlocked position, whereas FIG. 24 illustrates the slide bar 32 in the locked position. FIG. 24 also shows the lock assembly 12 applied to the overbag 14 (shown with the optional zipper closure 260). To provide a user with a visual indication of the position of the lock assembly 12, the slide bar 32 has position-related indicia that are selectively visible to the user depending upon the particular position. For example, FIG. 20 illustrates the unlocked icon 132 formed on the slide bar 32. The unlocked icon 132 is visibly exposed relative to the front housing section 28 only when the slide bar 32 is in the unlocked position or in an optional initial position that is highly proximate the unlocked position (as a point of reference, relative to the orientation of FIG. 20, in the closed position, the slide bar 32 is moved slightly leftward of the initial position illustrated). FIG. 24 reflects the locked icon 134 formed on the slide bar 32 that is visibly exposed only when the slide bar 32 is in the locked position. Due to the importance of ensuring that the slide bar 32 has been fully transitioned to the locked position, otherwise corresponding to the combination set state and/or the final securement mode to the overbag 14 (i.e., it may be possible for a user to visually see a portion of the locked icon 134 when the slide bar 32 has not been completely transitioned to the locked position), in some embodiments, the slide bar further carries the confirmation indicia 136 (e.g., indicator dots) that are only visible in the set indicator recess 104 formed by the front housing section 28. To permanently set the combination code into the lock assembly 12, the user must set the desired code characters 224 in alignment with the alignment feature 88 by manipulating the outer wheels 38. Once the desired code is aligned, the user must press the slide bar 32 toward the locked position (as indicated by the visibility of the locked icon 134) until the indicator dots 136 are completely visible. This ensures that the internal mechanism has travelled far enough to permanently set the unique identifier code into the lock assembly 12 (e.g., as part of the combination setting stage of operation in transitioning from the combination unset state to the combination set state) by fully coupling the inner wheels 36 with the outer wheels 38. Once this process has been completed, the lock assembly 12 can be attached to the overbag 14 by moving the slide bar 32 to the unlocked position and following the procedure detailed in the description for FIG. 21 above.

Figure 25:
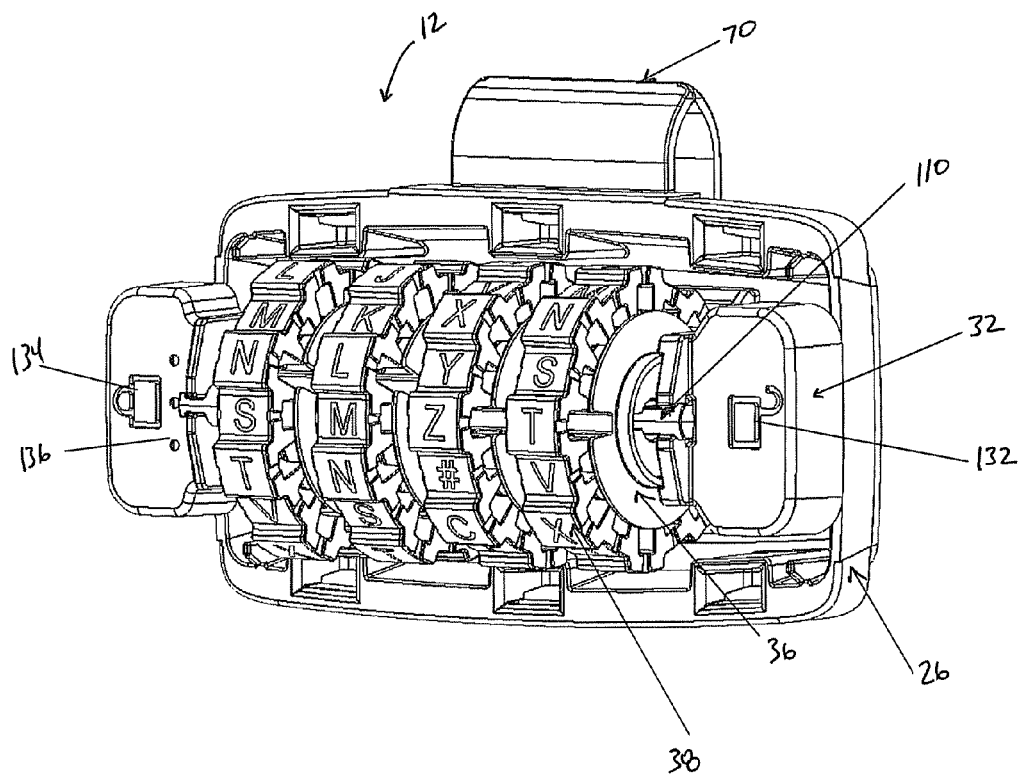
FIG. 25 is a front perspective view of the lock assembly of FIG. 1 with a front housing section removed to show internal components.

A detailed view of the internal components of the lock assembly 12 is shown in FIG. 25. In this view the front housing section 28 is hidden from view to allow a clear view of the internal components. The rear housing section 26 acts as the platform for the slide bar 32, which in turn supports the key pin 110, inner wheels 36 and outer wheels 38. These components comprise the main combination setting mechanism of the lock assembly 12, which can be seen in more detail in FIG. 26. With reference to FIGS. 25-28, each of the outer wheels 38 is co-axially disposed over a respective one of the inner wheels 36. The inner wheels 36, in turn, are co-axially disposed over the key pin 110 that is otherwise statically maintained by the slide bar 32. In this regard, the inner wheels 36 each form the inner keyway or notch 204 sized to receive the key feature or shoulder 180 that projects radially from the cylindrical pin body 170.

Figure 26:
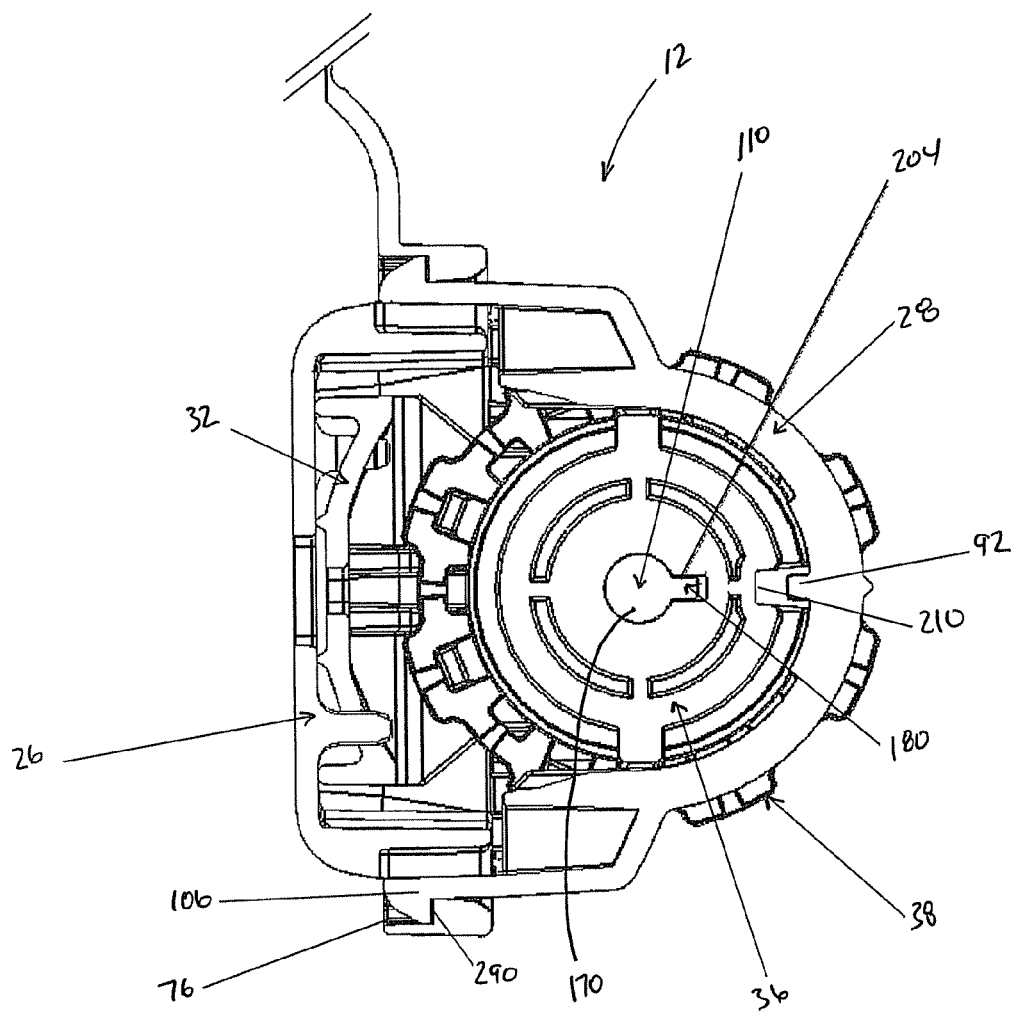
FIG. 26 is a cross-sectional view of the lock assembly of FIG. 1, illustrating an internal wheel anti rotation tab component preventing rotation of an internal wheel component when dialing a code and prior to setting a combination to the lock assembly.

FIG. 26 shows a cross section of the lock assembly 12 revealing details of the front housing section 28, the key pin 110 and one of the inner wheels 36 in accordance with some embodiments of the present disclosure. When initially dialing in the matching unique identifier code to correspond with the unique code provided with the system 10 (e.g., on the unique identifier label set 16 (FIG. 1)), the user will manipulate the outer wheels 38. Before the unique identifier code is set in to the lock assembly 12 (i.e., the slide bar 32 in the unlocked position), the inner wheels 36 are not coupled with the corresponding outer wheels 38, thus allowing the outer wheels 38 to be freely rotated without rotating the internal keyway 204. This allows the key pin 110 with its key features 180 and the slide bar 32 to freely translate. To prevent the rotation of the inner wheels 36, and thusly the internal keyways 204, the front housing section 28 is equipped with the internal wheel anti rotation tabs 92 that engages in the external keyway 210 on the inner wheel 36.

Also shown in FIG. 26 are two of the snap legs 106 that serves as an attachment means between the front housing section 28 and the rear housing section 26. To accomplish this attachment, the snap leg or leg portion of the front housing section 28 are inserted into the snap leg pockets 76 on the rear housing section 26. The snap leg 106 is inserted until the head portion thereof deflects and moves past a snap ledge 290 at which point the head will snap back to its relaxed position providing an interference fit between the two components.

Figure 27:
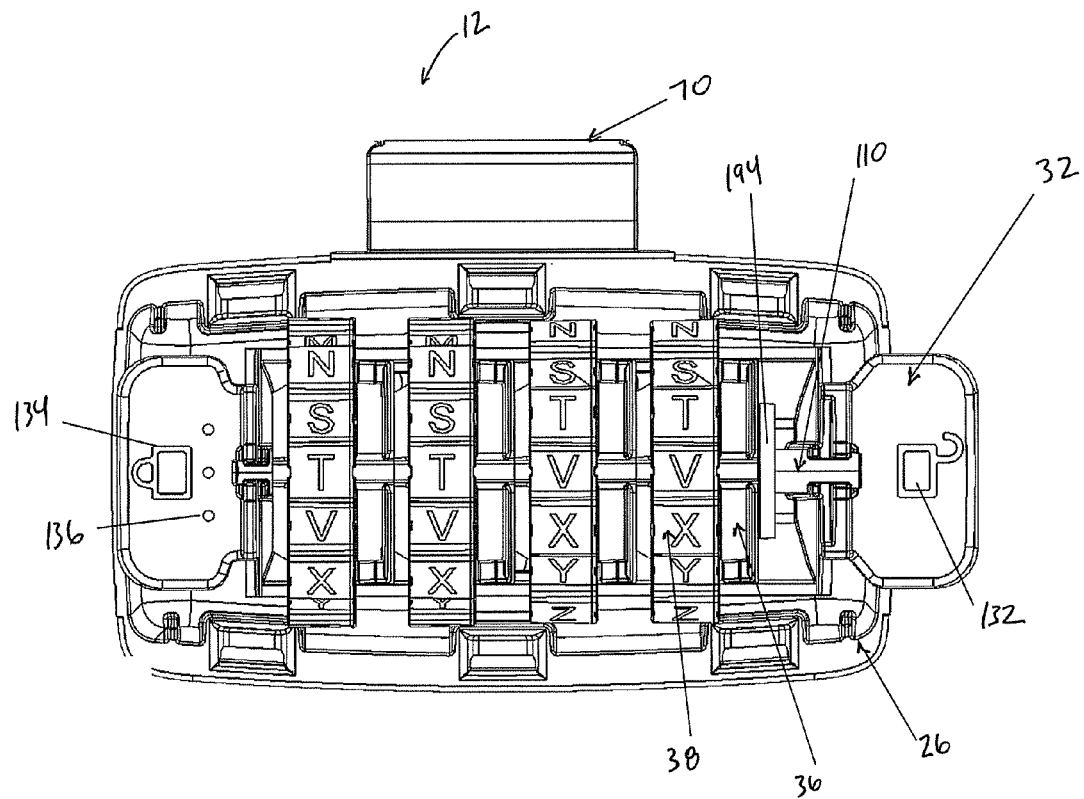
FIG. 27 is an enlarged front view of the lock assembly of FIG. 1 with a front housing component removed to show internal wheel components not yet coupled with external wheel components.

FIG. 27 is a front view of the lock assembly 12, again with the front housing section 28 hidden from view for clarity of the internal components. When the unique identifier code has been dialed in with the outer wheels 38, the user will press the slide bar 32 from the unlocked position (or the optional initial position) toward the locked position. The positions are indicated by the visibility of either the locked icon 134 or the unlocked icon 132 outside of the front housing section 28 (not shown in FIG. 27) as described above. When pressing the slide bar 32 it will translate until it comes into contact with the internal wheel anti rotation ring 194 or other such portion of the inner wheels 36 and due to the directly adjacent placement of the inner wheels 36 they will all be forced to translate on the key pin 110 and become coupled to the corresponding outer wheels 38. The outer wheels 38 are held in place during this motion by the front housing section 28 (not shown in FIG. 27).

Figure 28:
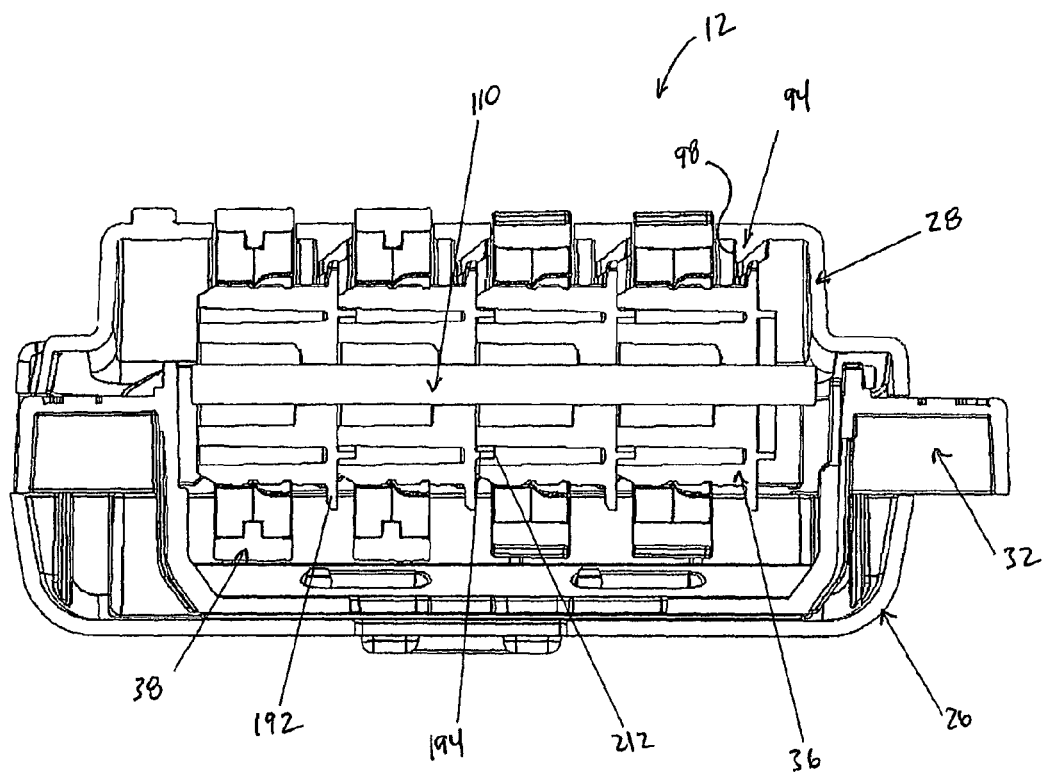
FIG. 28 is a cross-sectional view of the lock assembly of FIG. 1 and illustrating internal wheel components on an opposite side of single use ramp components on a rear side of a front housing section.

FIG. 28 consists of a cross-section of the lock assembly 12. In this cross-section, the single use ramps 94 on a back side of the front housing section 28 are visible. When setting the unique identifier code into the lock assembly 12, the user aligns the code using the outer wheels 38 and then presses the slide bar 32 toward the locked position. This forces the slide bar 32 into contact with the inner wheels 36 forcing internal wheel flanges 192 over the single use ramps 94. Once the inner wheels 38 have been pushed over or beyond the corresponding single use ramp 94 (i.e., the flange 192 abuts the ramp stop surface 98), they are permanently coupled with the corresponding outer wheel 38. This is the mechanism that enables the lock assembly 12 to act as a one time user settable combination lock, permanently associated with the single unique identifier code.

After this point, when the user rotates the outer wheels 38 they will also rotate the inner wheels 32. When the inner wheels 36 are rotated, the internal keyways 204 are also rotated, thus preventing the translation of the key pin 110 and the slide bar 32 from the locked position to the unlocked position. It is for this reason that after setting a combination into the lock assembly and applying it to the overbag 14 (FIG. 1), the user would complete the lock assembly 12 application process by moving the slide bar 32 to the locked position and then scrambling the outer wheels 36 (i.e., incorrectly entered code arrangement), and therefore the inner wheels 38 and internal keyways 204. Placing the lock assembly 12 in this operational mode prevents the lock assembly 12 from being removed from the overbag 14 until the correct unique identifier code is entered.

Figure 29:
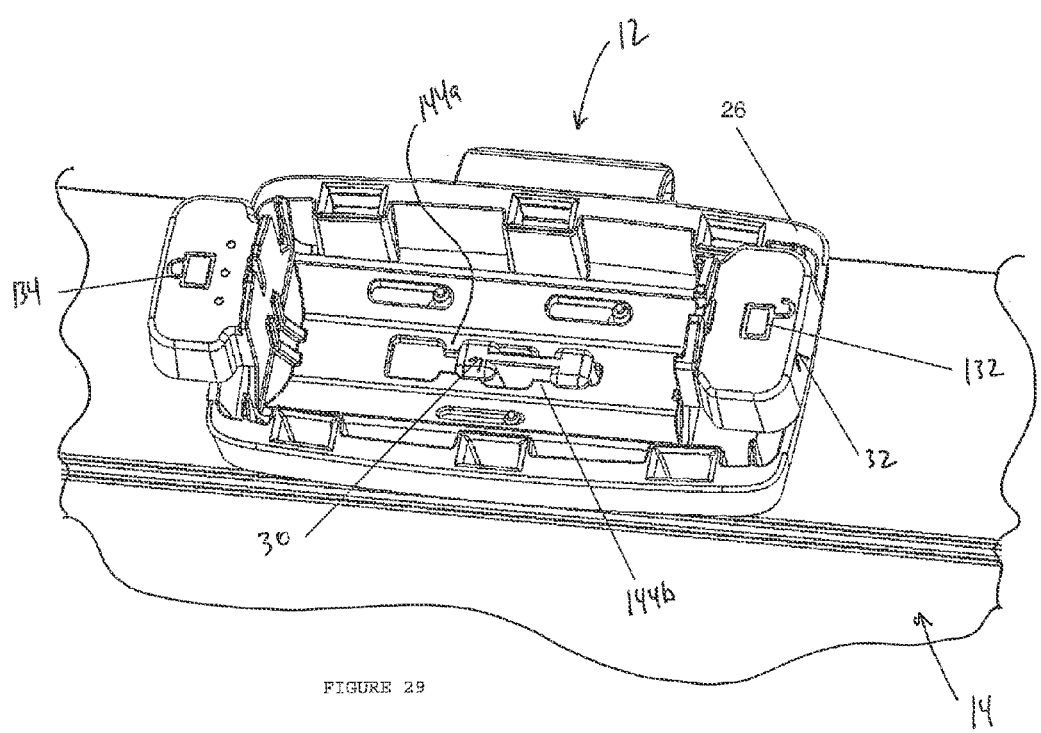
FIG. 29 is an enlarged, perspective view of a portion of the lock assembly of FIG. 1 in a locked position, and illustrating a lock plate component held captive by slide bar locking tabs in the locked position.

FIG. 29 shows a perspective view of the slide bar 32 and the rear housing section 26 with the back plate 40 (hidden in the view) rotated into the closed configuration. The front housing section 28, the outer wheels 38, the inner wheels 36 and the key pin 110 are all removed for clarity. The slide bar 32 is in the final position such that the capture slot lock tabs 144a, 144b are blocking the movement of the lock post 30. The slide bar 32 will be held in this captive position until the correct unique identifier code is entered into the lock assembly 12 via the outer wheels 38 to align the inner wheel internal keyways 204 to allow the slide bar 32 and the key pin 110 to move to the unlocked position.

With additional reference to FIG. 10A, one purpose of the internal wheel anti rotation ring 194 is to prevent the rotation of the inner wheel 36 when an axial force is applied to the slide bar 32 when the incorrect unique identifier code has been dialed in with the outer wheels 30 (FIG. 2A) after the lock assembly 12 (FIG. 1) has been set and locked. When an axial force is applied to the slide bar 32 in the final position with the incorrect unique identifier code dialed in to the outer wheels 38, it translates the key pin 119 (FIG. 28) into contact with the interior shelf 206 of the inner wheels 36. After contacting the interior of the interior shelf 206, the inner wheels 36 themselves are translated until the flange 192 contact the backside stop surface 98 of the single use ramps 94 (shown in FIG. 28). During this translation, the slide bar lock tabs 144a, 144b (FIG. 29) are also translating and show lessening interference with the post 30 (FIG. 29). To prevent the further reduction of this interference due to the lateral rotation of the inner wheels 36, the internal wheel anti rotation rings 194 are coupled with the internal wheel anti rotation engagement groove 212 (FIG. 10C) of the adjacent inner wheel 36 when assembled on the key pin 110 (FIG. 28) and placed into the slide bar 32. This interlocking construction limits the amount of lateral rotation of the inner wheels 36, the translation of the key pin 110 and ultimately the slide bar 32 and locking tabs 144a, 144b, thus maintaining their interference with the post 30 to reduce the likelihood of the lock assembly 12 being forced to unlock or move to the unlocked position when the incorrect unique identifier code has been entered.

With reference between FIGS. 1-29, operation of the system 10 is summarized as follows. The lock assembly 12 is initially provided in the combination unset state and the unlocked position (or optionally the initial position). With the slide bar 32 in the unlocked position or the initial position, the unique code is entered as the combination for the lock assembly 12 by rotating the outer wheels 38. The slide bar 32 is transitioned to the locked position, linking the outer wheels 38 with the inner wheels 36 and establishing the so-entered code as the combination for the lock assembly 12 in the now-achieved combination set state. The slide bar 32 is then transitioned back toward the unlocked position. In this regard, once the inner wheels 36 have been translated over the single use ramps 94, the lateral motion of the slide bar 32 is constrained and it can never fully move back to the initial position; instead, the slide bar 32 is translated to the unlocked position. As a point of reference, once the combination has been established, returning the slide bar 32 to the unlocked position does not "clear" or otherwise obliterate the set combination; instead, once set, the combination for the lock assembly 12 cannot be changed). With the slide bar 32 in the unlocked position, the lock assembly 12 is then applied to the overbag 14 including the post 30 being inserted within the rear housing section 26. The slide bar 32 is then moved to the locked position to capture the post 30. In connection with this movement of the slide bar 32 to the locked position, the lock assembly 12 can then be transitioned to the secured operational mode by "scrambling" the outer wheels 38 (i.e., transitioning to the incorrectly entered code arrangement), thereby securing the contents of the overbag 14. Subsequently, the lock assembly 12 can only be transitioned back to the unlocked position (and contents of the overbag 14 accessed) if the correct code is entered at the outer wheels 38 (i.e., the correctly entered code arrangement) to permit movement of the slide bar 32 back to the unlocked position.

Figure 30:
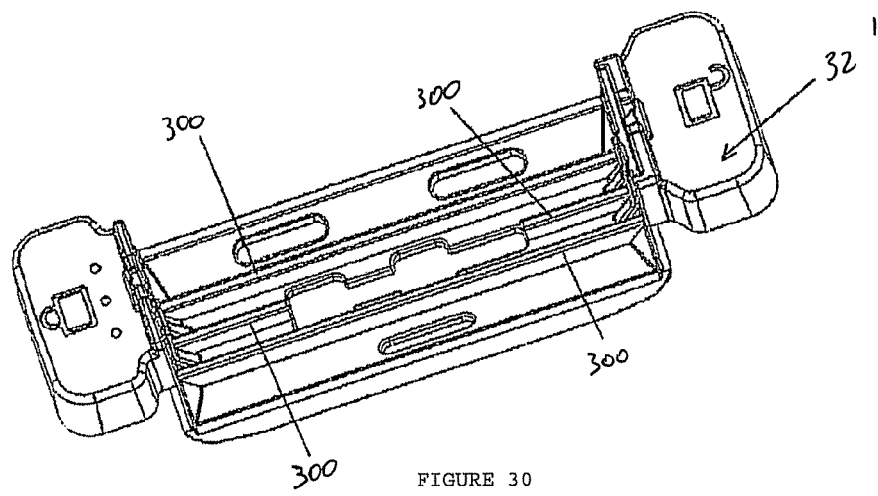
FIG. 30 is a front perspective view of an alternate slide bar useful with the lock assembly of FIG. 1 and including anti-deflection support ribs.

FIG. 30 shows a perspective view of an alternate embodiment slide bar 32'. This alternate embodiment adds a series of support ribs 300.

Figure 31:
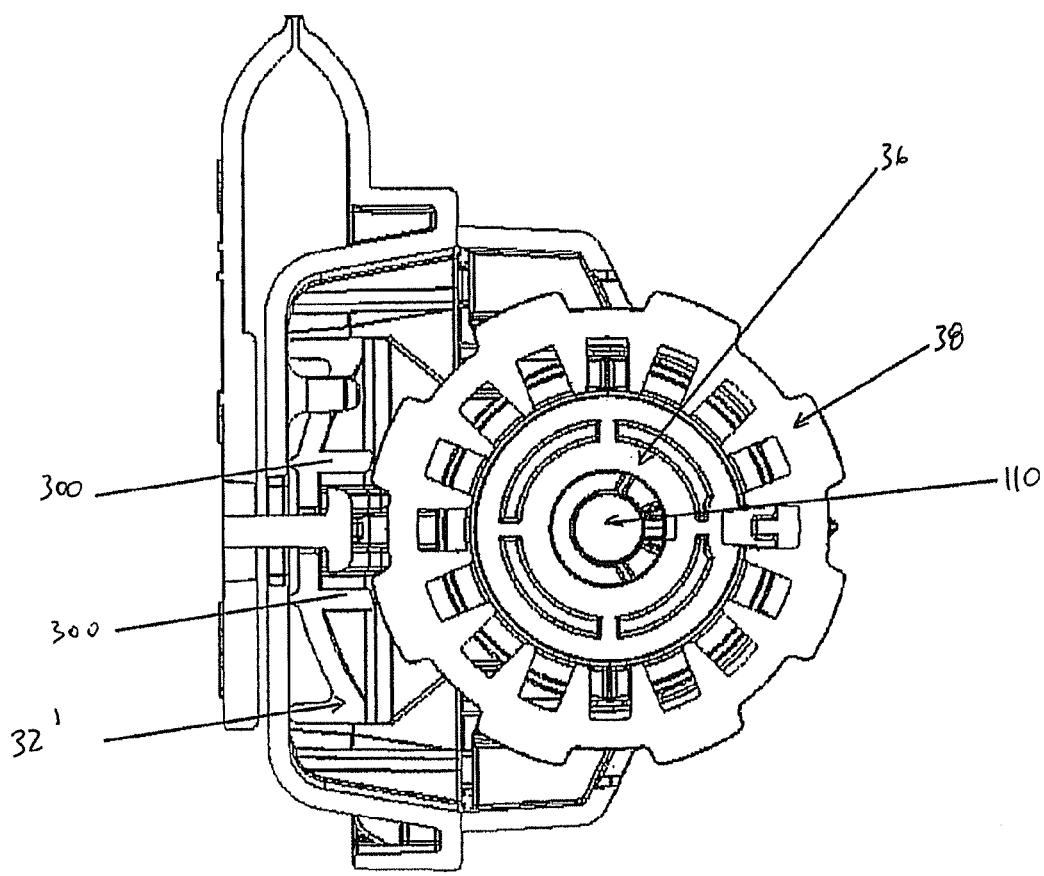
FIG. 31 is a cross-sectional view of a portion of another system in accordance with principles of the present disclosure and including an alternative lock assembly including the slide bar of FIG. 30 arranged to minimize key pin and external wheel component deflection.

FIG. 31 shows a cross-section of the lock assembly 12 with the support ribs 300 positioned to help resist the deflection of the key pin 110 by supporting the external wheels 30 when the slide bar 32' is attempted to be moved from the locked position with the incorrect unique identifier code entered. The lateral rotation of the inner wheels 36 also moves the outer wheels 38 due to the two components being coupled together after the code has been set in to the lock assembly 12. Similar to the inner wheel 36 lateral rotation described previously, this deflection of the outer wheels 38 and the key pin 110 can result in unwanted translation of the slide bar 32 which reduces the interference between the lock tabs 144a, 144b and the overbag lock post 30 (FIG. 29). The support ribs 300 help to minimize this unwanted slide bar 32 translation.

Although the present disclosure has been described with reference to preferred embodiments, those skilled in the art will recognize that changes can be made in form and detail without departing from the spirit and scope of the present disclosure. Such alternative examples include, but are not limited to the following:

Lock assemblies of the present disclosure could be attached to any container that is desired to be secured such as a rigid box, cooler, pneumatic tube carrier, or any other form other than an overbag and/or can be attached directly to the overbag or built in to the structure. With these and other embodiments, the post component provided above can be an integral component of the container. A plain or zip-top bag could be used interchangeably for the overbag 14. The lock assemblies of the present disclosure could be made to be re-usable by allowing a simple reset mechanism to allow the unique identifier code from a different unique identifier label set to be entered by allowing the inner wheel flanges to travel back to the other side of the single use ramps. The lock assemblies of the present disclosure could be made to be sterilizable by using a material such as a metal or other suitable material that would withstand the sterilization process conditions. In yet other embodiments, one or more features of the lock assemblies of the present disclosure can be electronically operated. For example, transverse movement of the slide bar component can be electronically actuated. In related embodiments, the lock assembly can be configured to receive a user-inputted code or combination electronically (e.g., RFID) and there may or may not be a visual display of the entered code; thus, the "correctly entered code" and "incorrectly entered code" arrangements described above are in reference to whether or not the lock assembly is, or is not, freely transitionable between the locked and unlocked positions, and may or may not entail the "display" of entered code.

The unique identifier machine readable codes described above as part of the unique identifier label set are linear in format but may also be 2D format or represented by an embedded non-optically readable transmission means such as a RFID chip. The outer wheels can be labeled with alphabetical, numerical, or special symbol characters. Along these same lines, more or less code characters may be used per outer wheel than the number shown to increase or decrease the total number of unique codes in system. More or less code characters (and therefore inner wheels and outer wheels on the lock assembly) may be used to increase total number of unique codes in the system. The back plate unit may be a separate component and not connected via a hinge as shown above.

The unique identifier label sets (or other unique code-bearing article) can contain both the unique identifier human readable code and the unique identifier machine readable code or only one or the other.

Other lock paradigms with internal mechanisms well known to those skilled in the art that require the alignment of dynamic characters can be utilized in a similar manner to the concepts presented herein. Additionally, aspects of the present disclosure relate to the use of the mechanical barrier recipient verification system to hold therapeutic materials—an example of which is shown in the enclosed figures to illustrate the use of the device. The use of the device for therapeutic materials is in no way limiting and the device can be used to secure other materials and materials of other sizes or shapes than the example shown or various types of objects that may otherwise require a specific verification of the correct recipient before granting access to the recipient.

What is claimed is:

1. A mechanical barrier recipient verification system comprising:
   a combination lock assembly including:
      a housing forming a trailing face and defining an aperture through the trailing face;
      a combination lock mechanism carried by the housing and configured to selectively receive and selectively capture a post inserted through the aperture, the lock mechanism configured to provide:
         a combination unset state in which a desired combination code is not established for the lock mechanism, and a combination set state in which the desired combination code is established for the lock mechanism,
an unlocked position in which the lock mechanism permits the post to freely enter or exit through the aperture, and a locked position in which the lock mechanism restricts movement of the post relative to the aperture,
a correctly entered code arrangement in which the lock mechanism is freely transitionable between the unlocked and locked positions, and an incorrectly entered code arrangement in which the lock mechanism is not freely transitionable between the unlocked and locked positions;
wherein following insertion of the post into the aperture and transitioning of the lock mechanism to the locked position, the lock mechanism is configured to retain the post in both of the correctly and incorrectly entered code arrangements;
and further wherein the lock assembly is configured such that the lock mechanism cannot be transitioned from the combination set state to the combination unset state.

2. The system of claim 1, further comprising:
a vessel apart from the lock assembly for containing an article;
wherein the lock assembly is configured to selectively secure the vessel.

3. The system of claim 1, wherein the lock assembly is configured such that the post can only be released from the lock assembly when the lock mechanism is in the unlocked position.

4. The system of claim 1, wherein the lock assembly further includes a back plate maintain the post and a hinge body extending between and interconnecting the back plate and the housing.

5. The system of claim 1, further comprising:
a receptacle configured to contain a patient-related article, the receptacle having an end portion terminating at an edge and including opposing walls that are selectively separable from one another to allow access to an interior containment region;
wherein the lock assembly is configured to form a mechanical barrier to separation of the opposing walls when the post is inserted through the receptacle and into the aperture and the lock assembly is in the locked position.

6. The system of claim 5, wherein the lock assembly further includes a back plate carrying the post and a connector body extending between and interconnecting the back plate with the housing, wherein the connector body is configured to establish a living hinge for pivoting movement of the back plate between a closed configuration in which the post is within the aperture and an open configuration in which the post is spaced from the housing, and further wherein the lock assembly forms a mechanical barrier to separation of the opposing wall with the back plate pivoted towards the housing to insert the post through the walls and into the aperture, and the receptacle edge being located between the post and the connector body such that the connector body prevents overt rotation of the receptacle relative to the lock assembly.

7. The system of claim 1, further comprising:
a unique identifier label set configured for coupling to a patient and presenting a unique code.

8. The system of claim 7, wherein the unique code provides the desired combination code.

9. The system of claim 1, wherein the lock mechanism includes:
at least one combination wheel pair mounted relative to the housing, the wheel pair defining a central axis and including an inner wheel and an outer wheel; and
a slide bar defining an intermediate section extending between opposing, first and second ends, the intermediate section defining a capture slot configured to selectively receive and selectively capture the post;
wherein the slide bar is mounted relative to the housing such that the intermediate section extends along the wheel pair in a direction of the central axis, the first end is adjacent the first side, and the second end is adjacent the second side.

10. The system of claim 9, wherein following insertion of the post into the aperture, transitioning of the lock mechanism to the locked position, and transitioning of the lock mechanism to the incorrectly entered code arrangement, the lock assembly is configured to release the post by consecutively:
arranging the outer wheel to a coded rotational position relative to the housing and corresponding to the desired combination code;
sliding the slide bar relative to the wheel pair,
withdrawing the post from the capture slot and the aperture.

11. The system of claim 9, wherein the post terminates at a head forming an enlarged segment and the capture slot has a shape defining a first section configured to permit passage of the enlarged segment and a second section configured to prevent passage of the enlarged segment, and further wherein:
the locked position includes the slide bar laterally positioned relative to the housing such that the second section is aligned with the enlarged segment,
the unlocked position includes the slide bar laterally positioned relative to the housing such that the first section is aligned with the enlarged segment.

12. The system of claim 9, wherein the outer wheel is rotationally uncoupled from the inner wheel in the combination unset state and is rotationally coupled to the inner wheel in the combination set state, and further where in the lock assembly is configured to transition from the combination unset state to the combination set state by:
moving the slide bar from a first position to a second position relative to the wheel pair and causing the inner wheel to become rotationally locked to the outer wheel.

13. The system of claim 9, wherein the inner wheel defines a flange, and the lock assembly further includes:
a ramp body disposed within the housing and associated with the inner wheel;
wherein the ramp body defines a ramp surface and a stop surface, the ramp body being arranged such that in transitioning from combination unset state to the combination set state, the flange region of the inner wheel travels along the ramp surface, and in the combination set state the flange abuts the stop surface.

14. The system of claim 9, further comprising:
a key pin connected to the slide bar and extending through the wheel pair along the central axis.

15. The system of claim 14, wherein the key pin includes a pin body and at least one shoulder projecting radially outwardly from the pin body, and further wherein the inner wheel defines a central passage sized to slideably receive the pin body and a keyway open to the central passage and sized to selectively receive the shoulder.

16. The system of claim 15, wherein the lock assembly includes a plurality of the wheel pairs and the key pin includes a corresponding plurality of the shoulders.

17. The system of claim 15, wherein the pin body is coaxially disposed within the passage, and further wherein the key pin is freely slideable relative to the inner wheel when the shoulder is aligned with the key way.

18. The system of claim 17, wherein the key pin is impeded from sliding relative to the inner wheel when the shoulder is not aligned with the key way.

19. The system of claim 15, wherein the key pin is assembled to the slide bar between the opposing, first and second ends, and further wherein the intermediate section is radially offset from the key pin.

20. The system of claim 19, wherein the pin body is fixed to the slide body such that the key pin translates with sliding movement of the slide bar.

\* \* \* \* \*